US012216074B2

(12) United States Patent
Seidl et al.

(10) Patent No.: US 12,216,074 B2
(45) Date of Patent: Feb. 4, 2025

(54) BIOSENSORS AND METHODS FOR DETERMINING ANALYTE CONCENTRATION IN THE KINETIC POTENTIAL REGION OF REDOX MEDIATORS

(71) Applicant: Pacific Diabetes Technologies, Inc., Portland, OR (US)

(72) Inventors: Thomas Seidl, Portland, OR (US); William Kenneth Ward, Portland, OR (US); Huan-Ping Wu, Portland, OR (US)

(73) Assignee: Pacific Diabetes Technologies, Inc., Portland, OR (US)

( * ) Notice: Subject to any disclaimer, the term of this patent is extended or adjusted under 35 U.S.C. 154(b) by 166 days.

(21) Appl. No.: 17/956,185

(22) Filed: Sep. 29, 2022

(65) Prior Publication Data

US 2024/0094156 A1    Mar. 21, 2024

Related U.S. Application Data

(60) Provisional application No. 63/251,191, filed on Oct. 1, 2021.

(51) Int. Cl.
  *G01N 27/26*  (2006.01)
  *A61B 5/145*  (2006.01)
  *A61B 5/1486*  (2006.01)

(52) U.S. Cl.
  CPC ......... *G01N 27/26* (2013.01); *A61B 5/14532* (2013.01); *A61B 5/1486* (2013.01)

(58) Field of Classification Search
  None
  See application file for complete search history.

(56) References Cited

U.S. PATENT DOCUMENTS 7,081,195 B2   7/2006  Simpson et al.
7,833,157 B2  11/2010  Gottlieb et al.
(Continued)

OTHER PUBLICATIONS

Jacobs, Peter G., et al., "Measuring Blucose at the Site of Insulin Delivery with a Redoc-Mediated Sensor", Biosens Bioelectron . Oct. 1, 2020;165:112221. doi: 10.1016/j.bios.2020.112221. Epub Apr. 29, 2020., Apr. 29, 2020, 1-9.
(Continued)

*Primary Examiner* — J. Christopher Ball
*Assistant Examiner* — John C Ball
(74) *Attorney, Agent, or Firm* — Blanchard Horton PLLC

(57) ABSTRACT

Methods and devices useful for determining the analyte concentration of a sample using output currents obtained from an input potential in the kinetic potential region of a redox mediator are disclosed. Preferably, the input potential used to generate the output currents from the kinetic potential region of the redox mediator is continually increasing with time after initiating the analysis. A method of selecting an initial input potential within the kinetic potential region of a redox mediator based on the sensitivity of an individual or batch of subcutaneously insertable test sensors also is described. A method of selecting an analysis input potential within the kinetic potential region of redox mediator based on the sensitivity of an individual subcutaneously inserted test sensor also is described where the analysis input potential is increased with insertion time.

62 Claims, 12 Drawing Sheets

(56) References Cited

U.S. PATENT DOCUMENTS

| | | | |
|---|---|---|---|
| 7,899,155 B2 | 3/2011 | Fadler | |
| 8,298,172 B2 | 10/2012 | Nielsen et al. | |
| 8,562,528 B2 | 10/2013 | Leach et al. | |
| 8,814,822 B2 | 8/2014 | Yodfat et al. | |
| 9,008,744 B2 | 4/2015 | Rose et al. | |
| 9,968,742 B2 | 5/2018 | Van Antwerp et al. | |
| 10,252,002 B2 | 4/2019 | Haider et al. | |
| 10,780,222 B2 | 9/2020 | Ward et al. | |
| 2008/0173552 A1* | 7/2008 | Wu | A61B 5/14546 374/E13.001 |
| 2012/0123230 A1 | 5/2012 | Brown et al. | |
| 2020/0245911 A1 | 8/2020 | Wu et al. | |
| 2020/0245912 A1 | 8/2020 | Wu | |
| 2021/0068724 A1 | 3/2021 | Wu | |
| 2021/0068725 A1 | 3/2021 | Wu | |
| 2022/0039700 A1 | 2/2022 | Wu et al. | |
| 2022/0039701 A1 | 2/2022 | Wu et al. | |
| 2022/0039702 A1 | 2/2022 | Wu et al. | |
| 2022/0039709 A1 | 2/2022 | Wu | |

OTHER PUBLICATIONS

Tschaikner, Mathias, et al., "Development of a Single-Site Device for Conjoined Glucose Sensing and Insulin Delivery in Type-1 Diabetes Patients", IEEE Trans Biomed Eng Jan. 2020;67(1):312-322. doi: 10.1109/TBME.2019.2919234. Epub May 27, 2019, May 27, 2019, 312-322.

Ward, W. Kenneth, et al., "An Amperometric Glucose Sensor Integrated into an Insulin Delivery Cannula: In Vitro and In Vivo Evaluation.", Diabetes Technol Ther Apr. 2017; 19(4):226-236. doi: 10.1089/dia.2016.0407. Epub Feb. 21, 2017., Feb. 21, 2017.

\* cited by examiner

BIOSENSORS AND METHODS FOR DETERMINING ANALYTE CONCENTRATION IN THE KINETIC POTENTIAL REGION OF REDOX MEDIATORS

REFERENCE TO RELATED APPLICATIONS

This application claims the benefit of U.S. Provisional Application No. 63/251,191 entitled "Biosensors and Methods for Determining Analyte Concentration in the Kinetic Potential Region of Redox Mediators" filed Oct. 1, 2021, which is incorporated by reference in its entirety.

BACKGROUND

The continuous in vivo sensing of analytes in biological fluids has become a routine operation in the field of medical devices. A specific example is continuous glucose monitoring (CGM) biosensors used in diabetes care that include a test sensor in electrical communication with a measurement device. CGM biosensors have the test sensor portion of the system inserted through the skin, thus residing subcutaneously and internally within the body, and surrounded by interstitial fluid. Unlike glucose monitoring systems that determine glucose concentrations in withdrawn blood samples using single-use disposable test strips, CGM systems determine glucose concentrations in a subject's interstitial fluid. However, as the output currents generated from the CGM device residing in the interstitial fluid are generally referenced against the corresponding known capillary blood glucose concentrations determined via single-use disposable test strips (BGM systems), the CGM determination is best characterized as representing a capillary blood glucose determination even though the test sensor resides in interstitial fluid. Interstitial fluid and blood glucose concentrations are strongly correlated.

The measurement device portion of the CGM system resides outside the body, thus controlling and recording signals from the inserted test sensor. Often, the measurement device additionally displays relevant data relating to the analysis and may communicate such data or be controlled by a remote device, such as a cellular phone or other computer. The measurement device generally includes a processor in electrical communication with a signal generator and a storage medium. The signal generator is in electrical communication with the electrodes of the inserted test sensor.

For CGM biosensors using electrochemical analyte analysis at the test sensor, miniaturized electrodes are often enclosed by an outer membrane layer. The electrode with its associated outer membrane layer is typically inserted subcutaneously.

Maintaining appropriate glucose concentrations in the blood is an important health consideration as individuals with diabetes are at risk of developing complications including kidney disease, eye disease, cardiovascular disease, and foot/nerve disease. It is typically more difficult to control blood glucose concentrations in those who require insulin treatment to maintain proper glucose concentrations in the blood as compared to those who do not require insulin to maintain proper blood concentrations. Individuals with Type 1 Diabetes (T1D) require insulin to maintain proper blood glucose concentrations. Many individuals with Type 2 Diabetes (T2D) do not require insulin to maintain proper blood glucose concentrations, instead relying on diet and non-insulin injected or oral medications.

Historically, T1D individuals have used standalone syringes with needles, or pen-style syringes for insulin delivery. However, as technology has improved, many are choosing to instead deliver insulin with a continuous insulin pump, which allows precise, regulated delivery of insulin 24 hours per day. Individuals who have chosen to use continuous insulin delivery pumps have also shown a desire and preference for CGM devices to have continuous knowledge of blood glucose concentrations throughout the day and night.

Daily life can be difficult for those who regularly use both an insulin pump and a CGM device as such individuals conventionally endure two continuously through-the-skin needles. As both the pump and the CGM devices require needles or the equivalent to continually reside internally within the body, having two such continuous skin penetrations increase the risk of pain at the entry sites, infection at the entry sites, and other side effects in relation to a single continuous skin penetration.

This multiplicity of continuous skin penetrations and the associated devices in electrical and/or fluid communication with the penetrations leads to a situation known as "device burden" for the user, which can lead to frustration, anger, and often causes an individual to choose either a continuous pump or CGM, rather than having the benefits of both. One example of a system addressing this "device burden" may be found in U.S. Pat. No. 10,780,222, which describes a system incorporating a continuous insulin pump with CGM through a single skin penetration.

The electrochemical test sensor of the CGM biosensor includes a working electrode, a counter electrode, and may include additional electrodes and bare conductors that contact the sample. It also is possible for an electrode, such as a counter electrode, to provide more than one electrochemical function, such as when a counter electrode provides a potential independent of the analysis, thus serving as a "counter-reference electrode". The analysis of the sample often has a chemical portion, such as the reaction of an enzyme with the analyte of interest, and an electrochemical portion where a redox mediator transfers electrons from a charged molecular species to the electrodes. For example, a test sensor configured to sense glucose may have a glucose specific enzyme, such as glucose oxidase or glucose dehydrogenase that reacts with glucose to provide analyte specificity to the electrochemical reaction with the redox mediator. In this instance, the analyte (glucose) molecules undergo the following cascaded and cycled reactions at the test sensor:

Glucose+Enzyme$_{(Ox)}$→Enzyme$_{(Red)}$+gluconolactone/gluconic acid

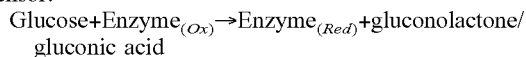

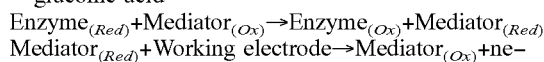

In this reaction series, Glucose in the sample reacts with Enzyme$_{(Ox)}$ (the oxidized form of enzyme) to form Enzyme$_{(Red)}$ (the reduced form of the enzyme) which then reacts with Mediator$_{(Ox)}$ (the oxidized form the mediator) to produce Mediator$_{(Red)}$ (the reduced form the mediator). The Mediator$_{(Red)}$ then transfers electron/s to the working electrode of the test sensor to regenerate Mediator$_{(Ox)}$, which may again react with the Enzyme$_{(Red)}$ to continue the reaction cycle. Depending on the nature of the mediator, a singe mediator molecule may transfer one or more electron to the electrode, and thus the "n" in the last equation may be greater than one. It is the electron/s released to the working electrode by the Mediator$_{(Red)}$ that is detected and quantified by the measurement device to determine the glucose concentration of the sample.

When the test sensor includes two electrodes the operation of the working electrode is under a constant input potential, which senses the analyte responsive signals, and is balanced electrochemically by the reaction at the counter electrode. The counter electrode also serves as the reference electrode and is thus a counter-reference electrode. The two-electrode system has the advantage of simplicity, is less demanding of subcutaneous physical space, and requires fewer connectors—all advantageous when the test sensor is intended for continuous subcutaneous use. However, the effective life span of the test sensor may be limited by the amount of redox material (such as silver chloride chemically adhered at the counter-reference electrode or to a dedicated reference electrode) that provides an independent reference potential to the measurement device or by the amount of redox mediator at the working electrode.

When the test sensor includes three electrodes the functions of the counter and reference electrodes are served separately by a dedicated counter electrode, which carries the major currents counter-balancing the electrochemical reactions at the working electrode, and a dedicated reference electrode, which draws very little current from the working electrode, but provides an independent and stable potential for the analysis. Additional working electrodes may be added to either a two- or three-electrode system to provide additional functionality to the test sensor.

When the test sensor resides inside the body and is in continuous contact with interstitial fluid, it can be advantageous to immobilize the enzyme and/or the redox mediator at or near the electrode surfaces. The enzyme may be immobilized at the electrode surface by cross-linking agents such as glutaraldehyde. The chemically active layer is then protected by an outer polymer layer. The redox mediator may be the natural oxygen molecules present in the sample or a non-natural redox mediator such as an osmium complex that is preferably immobilized at or near the electrode surfaces.

For a glucose test sensor relying on the glucose oxidase enzyme to provide a glucose specific sample analysis and the natural redox mediator oxygen, the product of the enzyme reaction is hydrogen peroxide. The advantage of such a hydrogen peroxide-based system is its simplicity where the chemically active layer only includes the enzyme. However, two disadvantages of such a system are the dependence on oxygen availability in the sample and the relatively high oxidation potential of hydrogen peroxide. While not a consideration for single-use disposable test sensors that analyze drawn blood samples, a subcutaneously inserted test sensor continually analyzing interstitial fluid as the sample can exhaust the oxygen available in the interstitial fluid near the inserted test sensor. In addition to oxygen depletion, the relatively high oxidation potential of hydrogen peroxide in relation to interferents in the interstitial fluid sample surrounding the test sensor results in non-analyte responsive output signals being generated from the interferents that are inseparable from the glucose responsive output signals. Such interferents include uric acid, acetaminophen, and ascorbic acid.

By switching from the relatively high oxidation potential of hydrogen peroxide to the relatively low oxidation potential non-natural mediators, the accuracy of the glucose analysis may be improved as non-analyte-responsive output signals are reduced. One example of such a lower oxidation potential, non-natural redox mediator is the osmium complex mediators, such as found in Heller, "Wired enzyme electrodes for amperometric determination of glucose or lactate in the presence of interfering substances", Anal. Chem. 1994; 66(15):2451-7. To reduce the intermittent problem of natural oxygen mediator exhaustion at the test sensor, the non-natural mediator may be linked with a polymer chain or the like to the electrode/s, thus increasing the local non-natural mediator concentration. Such electrode immobilized mediator systems may be referred to as polymer-linked-mediator (PLM), or redox-mediator-polymer (RMP) systems. Immobilizing the mediator near the electrode surface can provide the added benefit of enhanced "recycling" between the electrode surface and the enzyme, thus increasing the available output signal in relation to non-immobilized mediators that can diffuse away from the electrode surfaces, especially when continuously residing in interstitial fluid.

The working electrode of a test sensor is generally in electrical communication with a potentiostat. Conventionally, the working electrode is operated by a potentiostat at a potential in or greater than the plateau oxidation potential of the redox mediator. This relatively high potential is used to ensure that all redox mediator that has undergone a redox reaction with the enzyme undergoes a redox reaction with the working electrode. Thus, the output signal from the working electrode is limited only by the diffusion rate of the mediator reaching the working electrode after exchanging electrons with the enzyme and has no dependence on partially oxidized or reduced redox mediator. In this situation, the output current measured between the working and counter electrodes is substantially independent of variation in the input potential applied between the electrodes by the measurement device as the input potential is at or greater than the plateau oxidation potential of the redox mediator. While the relatively high input potential provides output currents with a substantially linear correlation to sample analyte concentrations, the relatively high input potential enhances the depletion rate of redox material at a counter-reference electrode and potentially increases the rate of membrane failure due to the pores in the membrane becoming blocked for the inserted test sensor.

While the output currents are substantially independent of the input potential when operating the working electrode at the plateau oxidation potential, conventional systems using more than one input potential have been described. For example, in columns seven and eight U.S. Pat. No. 7,081,195 discloses measuring current values at multiple input potential settings, specifically by switching potentials between 0.4 V and 0.6 V. The higher input potential is used to determine the analyte concentration while the lower input potential is used to assess the "quality" of the analyte measurement and to identify interference in the output signals.

In another example, in column 68, line 35, U.S. Pat. No. 7,899,155 discloses applying a 0.6 V input potential for normal operation of the biosensor and increases the input potential by an additional 0.05 V to 0.4 V above the normal potential to generate additional oxygen, so the system does not exhaust the available natural mediator. Columns 35 and 36 of U.S. Pat. No. 9,008,744 disclose using high and low input potentials to generate different responses and to analyze the relaxation kinetics for test sensor information. This patent also describes initially applying short pulses of alternating high and low potentials before the analysis of the analyte begins and even very short (milli-second) pulses for sensor initialization and electrode conditioning. (Cols. 38, 39, 40). U.S. Pat. Pub. No. 2020/0245911 and U.S. Pat. Pub. No. 2020/0245912 disclose using probing potential modulation sequences (potential steps different from the normally constant applied voltage at the plateau oxidation potential region) to generate useful information for error compensation. In combination, these references disclose using input potentials that are both higher and lower than the plateau oxidation potential of the redox mediator; however, none use input potentials lower than the plateau oxidation potential of the redox mediator to directly determine the analyte concentration, instead using the lower input potentials for compensation and other ancillary portions of the analysis.

Calibration of a specific or a specific batch of CGM test sensors for proper operation with the measurement device is desired to reduce the number of "manual" calibrations requiring conventional drawn blood testing, with the associated finger-sticks, to obtain blood for single-use disposable test strips. A significant factor relating to the different sensitivities between individual or batches of CGM test sensor arises from manufacturing variation in the test sensors that leads to a different manufactured sensitivity for individual or batches of test sensors. Unfortunately, reducing manufacturing variance, and thus differences in manufactured sensitivity between test sensors, often results in lowering production yield of the test sensors and thus increasing cost. Alterations in the analysis method or data manipulation performed in the measurement device also have been attempted to alleviate differences in the test sensors' sensitivity distribution. However, the requirement of frequent CGM calibration with conventional blood-based, single-use disposable test strips remains.

As can be seen from the above description, there is an ongoing need for simple and efficient systems, devices, and methods for continually monitoring analyte concentrations in interstitial fluid, especially in the context of extending the subcutaneous insertion life of the test sensor and being able to effectively use test sensors with relatively large sensitivity variance due to manufacturing variability. The systems, devices, and methods of present invention overcome at least one of the disadvantages associated with conventional CGM systems, devices, and methods.

SUMMARY

In one aspect, the invention provides a method for determining an analyte concentration in a sample, the method comprising: applying high and low calibration input potentials to a subcutaneously inserted test sensor, where the high and low calibration input potentials are within a kinetic potential region of a redox mediator of the test sensor; measuring output currents responsive to the high and the low calibration input potentials from the subcutaneously inserted test sensor; determining a regression sensitivity relationship from the measured output currents responsive to the high and the low calibration input potentials; determining a first analysis input potential within the kinetic potential region of the redox mediator from the regression sensitivity relationship; applying the first analysis input potential to the subcutaneously inserted test sensor; modifying a first redox state to a second redox state of the redox mediator, where a concentration of the first redox state of the redox mediator is responsive to an analyte concentration in a sample; measuring output currents responsive to the first analysis input potential from the subcutaneously inserted test sensor; determining the analyte concentration of the sample in response to the measured output currents responsive to the first analysis input potential; and reporting the determined analyte concentration to a user.

In another aspect of the invention, there is a method of determining an initial input potential for a test sensor based on the manufactured sensitivity of the test sensor, for performing an analysis of a sample with the test sensor, the method comprising: applying high and low calibration input potentials to a test sensor contacting a sample, where the high and low calibration input potentials are within a kinetic potential region of a redox mediator of the test sensor; measuring output currents responsive to the high and the low calibration input potentials from the test sensor; determining a regression sensitivity relationship from the measured output currents responsive to the high and the low calibration input potentials using a known laboratory analyte concentration or a reference analyte concentration of the sample by modifying the measured output currents responsive to the high and the low calibration input potentials with the known laboratory analyte concentration of the sample; determining an initial input potential by multiplying a slope from the regression sensitivity relationship by a selected sensitivity and combining with an intercept from the regression sensitivity relationship.

In another aspect of the invention, there is a method of determining an initial input potential for a test sensor based on the manufactured sensitivity of the test sensor, for performing an analysis of a sample with the test sensor, the method comprising: applying high and low calibration input potentials to multiple test sensors contacting a sample, where the high and low calibration input potentials are within a kinetic potential region of a redox mediator of the test sensor; measuring output currents responsive to the high and the low calibration input potentials from the multiple test sensors; determining a high calibration input potential regression relationship and a low calibration input potential regression relationship from the output currents measured from the multiple test sensors and a known laboratory analyte concentration or a reference analyte concentration to obtain a high calibration input potential change rate and a low calibration input potential change rate; determining pair point relationship for a single test sensor from a RS value of the single test sensor, a selected sensitivity, and the intercept of the high and low calibration input potential regression relationships; determining a change rate relationship from the high and low calibration input potentials and the high and low calibration input potential change rates; and determining an initial input potential for the test sensor from the change rate relationship and a single test sensor change rate determined from the pair point relationship.

In another aspect of the invention, there is an analyte measurement device, comprising: a processor in electrical communication with a signal generator and a storage medium, where the processor is capable of measuring output currents responsive to input potentials, where the signal generator is capable of providing the input potentials to the working and counter electrodes of a test sensor and transferring output currents responsive to the input potentials from the test sensor to the processor; where the processor is capable of instructing the signal generator to apply high and low calibration input potentials to the test sensor, where the high and low calibration input potentials are within a kinetic potential region of a redox mediator of the test sensor; where the processor is capable of measuring output currents responsive to the high and the low calibration input potentials; where the processor is capable of determining a regression sensitivity relationship from the measured output currents responsive to the high and the low calibration input potentials; where the processor is capable of determining a first analysis input potential within the kinetic potential region of the redox mediator from the regression sensitivity relationship; where the processor is capable of instructing the signal generator to apply the first analysis input potential to the test sensor; where the processor is capable of measuring output currents responsive to the first analysis input potential from the test sensor; where the processor is capable of determining the analyte concentration of a sample in response to the measured output currents responsive to the first analysis input potential; and where the processor is capable of reporting the determined analyte concentration to a user.

In another aspect of the invention, there is a biosensor system for determining an analyte concentration in a sample, comprising: a test sensor comprising working and counter electrodes and a redox mediator; a measurement device comprising a processor in electrical communication with a signal generator and a storage medium, where the working and the counter electrodes are in electrical communication with the signal generator; where the processor is capable of measuring output currents responsive to input potentials from the test sensor, where the signal generator is capable of providing the input potentials to the working and the counter electrodes and transferring output currents responsive to the input potentials from the working and the counter electrodes to the processor; where the processor is capable of instructing the signal generator to apply high and low calibration input potentials to the working and the counter electrodes, where the high and low calibration input potentials are within a kinetic potential region of the redox mediator; where the processor is capable of measuring output currents responsive to the high and the low calibration input potentials; where the processor is capable of determining a regression sensitivity relationship from the measured output currents responsive to the high and the low calibration input potentials; where the processor is capable of determining a first analysis input potential within the kinetic potential region of the redox mediator from the regression sensitivity relationship; where the processor is capable of instructing the signal generator to apply the first analysis input potential to the working and the counter electrodes; where the processor is capable of measuring output currents responsive to the first analysis input potential from the working and the counter electrodes; where the processor is capable of determining the analyte concentration of a sample in response to the measured output currents responsive to the first analysis input potential; and where the processor is capable of reporting the determined analyte concentration to a user.

BRIEF DESCRIPTION OF THE FIGURES

The invention can be better understood with reference to the following drawings and description. The components in the figures are not necessarily to scale, emphasis instead being placed upon illustrating the principles of the invention.

DETAILED DESCRIPTION

Methods and devices useful for determining the analyte concentration of a sample using output currents obtained from an input potential in the kinetic potential region of a redox mediator are disclosed. Preferably, the input potential used to generate the output currents from the kinetic potential region of the redox mediator is continually increasing with time after initiating the analysis. A method of selecting an initial input potential within the kinetic potential region of a redox mediator based on the sensitivity of an individual or batch of subcutaneously insertable test sensors also is described. A method of selecting an analysis input potential within the kinetic potential region of redox mediator based on the sensitivity of an individual subcutaneously inserted test sensor also is described where the analysis input potential is increased with insertion time.

The described methods and devices determine the appropriate input potentials within the kinetic potential region of a redox mediator to provide linearity or near-linearity, thus substantial linearity, over the desired analyte concentration range of the sample while simultaneously correcting for differences in test sensor selectivity and subjecting the test sensor to the lowest input potential sufficient to operate the test sensor to extend the useful life of the inserted test sensor. These considerations may be addressed on a test sensor by test sensor basis or through a combination of data obtained from a group of test sensors and an individual test sensor, both in the laboratory and after subcutaneous insertion. The described methods also allow the test sensor to provide accurately correlatable output currents significantly more quickly after subcutaneous insertion of the test sensor than conventional methods using inserted test sensors for CGM.

A significant benefit of matching the input potential to the manufactured sensitivity of the test sensor is that if a fixed higher input potential were used with the higher sensitivity test sensors after insertion, the useful life of the higher sensitivity test sensors would be significantly reduced. Thus, by appropriately matching the input potential to the sensitivity of the test sensor before and during the analysis, and thus using lower input potentials with more sensitive test sensors, the useful lifespan of higher sensitivity subcutaneously inserted test sensors may be extended.

Figure 1:
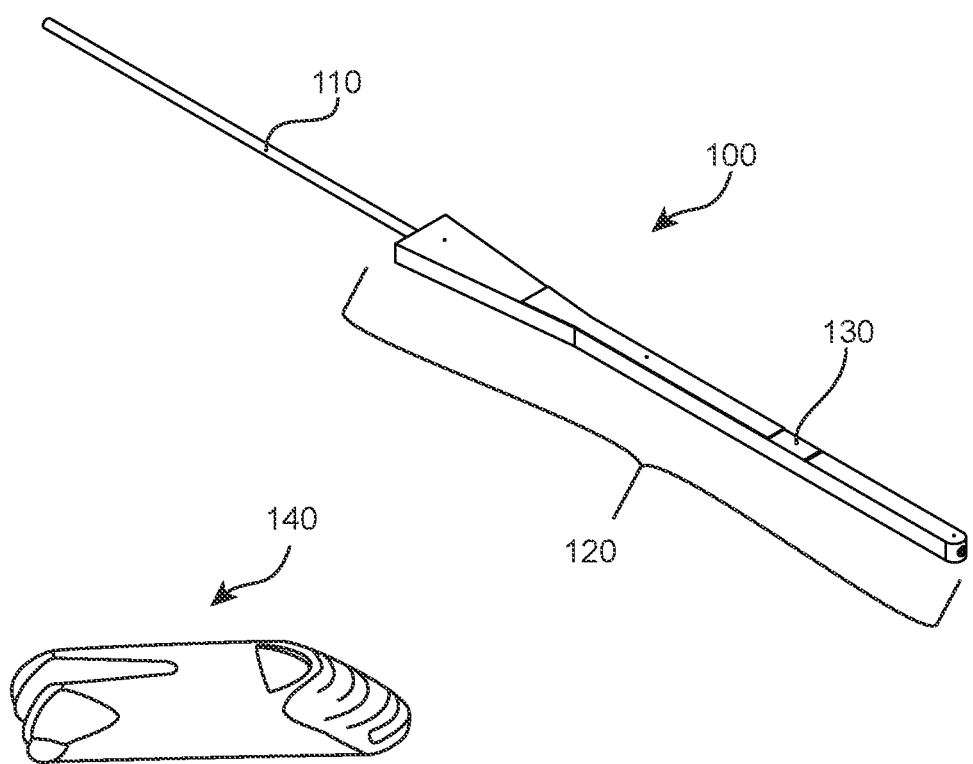
FIG. 1 represents a test sensor for subcutaneous glucose concentration determination integrated with an insulin delivery cannula passing through the center of a test sensor structure and a measurement device.

FIG. 1 represents a test sensor 100 for subcutaneous glucose concentration determination integrated with an insulin delivery cannula 110 passing through the center of a test sensor structure 120 and a measurement device 140. Working electrode 130 is exposed to interstitial fluid when the test sensor 100 is inserted through the skin and resides subcutaneously within the body. Opposite the working electrode 130 on the "bottom" surface resides a counter electrode (not shown), which serves as a counter-reference electrode as the counter electrode includes a redox material, such as silver chloride (AgCl), adhered to the electrode, such as when the conductor on which the redox material is adhered is silver metal (Ag). The redox material provides an independent potential during the analysis of the interstitial fluid sample. When subcutaneously inserted, the test sensor 100 creates an electrical circuit between the working electrode 130, the counter electrode, and the interstitial fluid sample. Other designs may be used for the test sensor 100. The measurement device 140 also is represented which can provide an input potential to and measure output currents from the test sensor 100. The measurement device 140 may have additional functionality.

The working electrode 130 includes an analyte specific enzyme and an immobilized redox mediator having a lower redox potential than the oxygen/hydrogen peroxide redox mediator. For glucose analysis, the analyte specific enzyme preferably is glucose oxidase or glucose dehydrogenase, with glucose oxidase being more preferred. The immobilized redox mediator is preferably osmium-complex based, with an osmium-ligand-polymer system where the osmium-complex redox mediator is covalently linked to the polymer being preferred. In addition to osmium metal based redox mediators, other useful metals for potential use as redox mediators include ruthenium, palladium, platinum, rhodium, iridium, cobalt, iron, and copper.

The measurement device 140 may be used to perform an analysis of the analyte in combination with the test sensor 100 when the test sensor 100 is subcutaneously inserted under the skin of a subject. The measurement device 140 includes electrical conductor contacts that electrically connect with the electrodes of the test sensor. The measurement device 140 may be activated manually, such as with a button, by electrical connection with the test sensor, or by the sample completing a circuit within the test sensor. For example, a relatively low potential of 50 mV may be applied between one or more electrodes of the test sensor 100 to determine that the test sensor is adequately inserted through the skin.

The measurement device 140 may have the processing capability to measure and correlate the electrical output measured from the test sensor 100 with the presence and/or concentration of one or more analytes in the sample. The measurement device 140 may communicate the measured electrical outputs to a secondary processing device such as a smartphone that correlates the electrical outputs to the presence and/or concentration of one or more analytes in the sample.

The measurement device 140 measures the electrical output from the test sensor as a current, as generated by amperometry. The measurement device 140 uses the measured output currents to quantify the analyte in the sample contacting the working and counter electrode pair. The measurement device 140 may be configured to apply a potential from −200 mV to +650 mV between the working and counter electrode pair of the test sensor, depending on the redox mediator. In the case of the osmium-complex based redox mediator (2-(4,4'dimethyl)-2,2'bipyridine-osmium chloride), the input potential may be from −150 mV to +200 mV. In the case of an oxygen/hydrogen peroxide redox mediator, the input potential may be from +100 to +600 mV. In the case of a ferrocene monocarboxylic acid redox mediator, a derivative of the ferrocene/ferrocenium redox couple, the input potential may be from +100 to +400 mV.

Figure 2A:
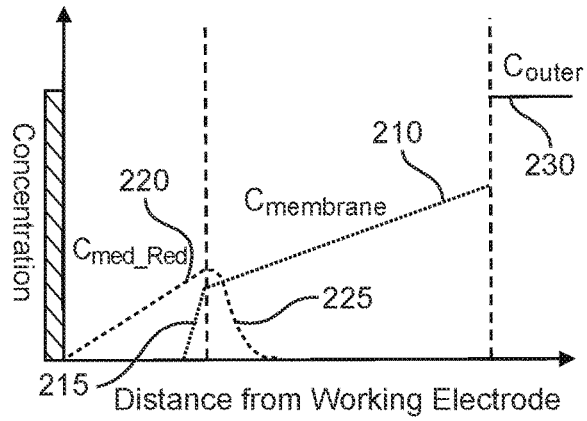
FIG. 2A represents a boundary condition generated in response to an input potential at the surface of a working electrode of a test sensor including glucose oxidase that relies on oxygen as a natural mediator.

FIG. 2A represents a boundary condition generated in response to an input potential at the surface of a working electrode of a test sensor including glucose oxidase that relies on oxygen as a natural mediator. The working and counter electrodes of the test sensor are isolated from the sample by a membrane having a thickness, where the thickness is often in the range of 10-50 micrometers (µm). The input potential applied between the working and counter electrodes of the test sensor is great enough to exceed the plateau oxidation potential of hydrogen peroxide, thus 0.55 V or greater vs. the potential of a Ag/AgCl reference electrode.

The X-axis represents increasing distance from the surface of the working electrode, while the Y-axis shows analyte concentration in the sample. The two vertical dashed lines on the graph define the first interface from the enzyme layer of the working electrode to the outer surface of the membrane, and the second interface between the outer surface of the membrane and the sample. The first interface is towards the working electrode where the space above the electrode occupied by the enzyme resides to the left, the space above the electrode occupied by the membrane is represented in the middle, and the sample residing outside of the membrane is to the right of the second interface. Outside of the membrane concentration 230 is the analyte concentration of the interstitial fluid sample. Within the membrane concentration 210 is the analyte concentration present within the thickness of the membrane. "Under" the membrane, where the enzyme resides, concentration of the reduced mediator 220 is shown as the enzyme converts the analyte to reduced mediator—hydrogen peroxide in this natural mediator system. The concentration of the reduced mediator 220 is responsive to the analyte concentration of the sample.

When the input potential is applied between the working and the counter electrodes, electrons are continually being transferred from the analyte to the enzyme, and then from the enzyme to oxygen as a mediator to generate the reduced mediator hydrogen peroxide, which is then oxidized at the working electrode. The analyte within the membrane concentration 210 forms an approximately linear gradient, which is driven by the enzyme reaction causing it to be consumed and drops to zero in the enzyme region "under" the membrane 215. As the natural mediator oxygen is not immobilized at the electrode, the reduced mediator concentration 220 "under" the membrane also diffuses back into the membrane creating a reduced mediator concentration 225 within the membrane.

The analyte is continuously being consumed at the working electrode, so the analyte is continually entering the membrane, where the rate of the analyte entering the membrane at the interface is greater than the rate of the analyte being consumed at the working electrode. This situation establishes a "diffusion-limited" rate of analyte consumption at and near the surface of the working electrode. For the diffusion-limited situation, the higher the analyte concentration in the sample, the higher the analyte concentration within the membrane, and thus the higher the redox mediator concentration gradient at and near electrode surface. This leads to a higher current, i.e., $i \propto dC_{med}/dx$, as shown by the near linear concentration gradient 220 near the electrode surface.

A key reason that electrochemical analysis is conventionally performed with output currents obtained from the diffusion-limited region after the plateau oxidation potential of the reduced mediator is exceeded is due to the relatively large output signals obtained from the region. The larger the output currents measured from the test sensor in response to the input potential, the greater the signal to noise ratio performance or "sensitivity" of the test sensor.

Figure 2B:
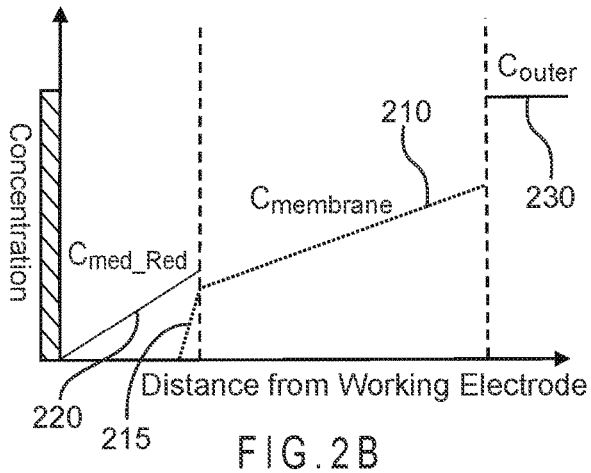
FIG. 2B represents another diffusion-limited boundary situation where the input potential is great enough to exceed the plateau oxidation potential of the reduced mediator, but where a non-natural immobilized osmium-complex mediator is used as opposed to oxygen.

FIG. 2B represents another diffusion-limited boundary situation where the input potential is great enough to exceed the plateau oxidation potential of the reduced mediator, but where a non-natural immobilized osmium-complex mediator is used as opposed to oxygen. The plateau oxidation potential of the reduced osmium-complex mediator starts at approximately +0.175 V and extends to about +0.3 V vs. an Ag/AgCl reference. Thus, in relation to FIG. 2A the reduced mediator concentration 225 within the membrane is absent as the mediator is covalently linked to the immobilized polymer system and cannot substantially diffuse into the membrane.

Figure 2C:
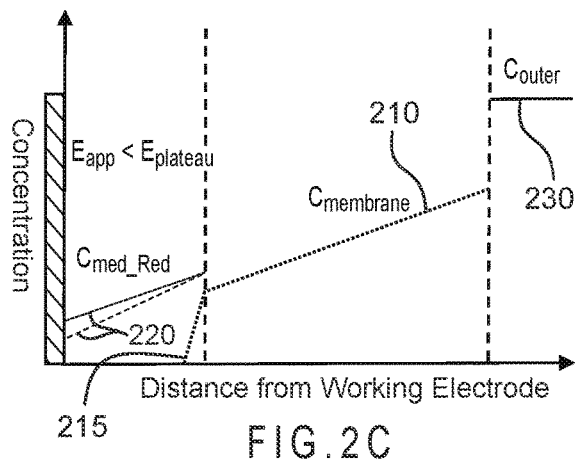
FIG. 2C represents a non-diffusion-limited boundary situation where the input potential is not great enough to exceed the plateau oxidation potential of the reduced mediator.

FIG. 2C represents a non-diffusion-limited boundary situation where the input potential is not great enough to exceed the plateau oxidation potential of the reduced mediator. As the input potential does not exceed the plateau oxidation potential of the reduced mediator, the kinetic potential region of the reduced mediator is being observed. As previously observed in FIG. 2B the reduced mediator is substantially absent from the membrane region due to immobilization. However, a significant departure from the FIG. 2A and FIG. 2B reduced mediator concentration is observed. First, the reduced mediator concentration relationship 220 does not start at zero concentration at the electrode surface because in the kinetic potential region of the redox mediator, the reduced and oxidized forms of the redox mediator coexist as the oxidation potential is lower than the plateau oxidation potential. Secondly, more than one relationship 220 is present to represent that multiple different input potentials may be applied in the kinetic potential region of the redox mediator to determine the analyte concentration of the sample. The oxidized redox mediator immobilized at the working electrode also does not diffuse substantially into the membrane.

Figure 3A:
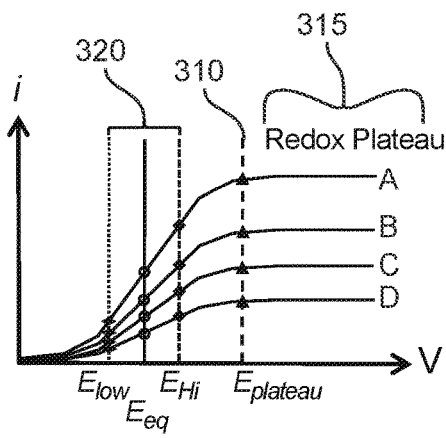
FIG. 3A represents current outputs as would be obtained at four different analyte concentrations (A, B, C, D) from input potentials exceeding and not exceeding the plateau oxidation potential of the reduced mediator.

FIG. 3A represents current outputs as would be obtained at four different analyte concentrations (A, B, C, D) from input potentials exceeding and not exceeding the plateau oxidation potential of the reduced mediator. Once the input potential exceeds the plateau oxidation potential of the reduced mediator represented by the $E_{plateau}$ vertical dashed relationship 310, the measured plateau oxidation potential output currents 315 are substantially "flat", and thus no longer change as the input potential continues to increase. In this flat potential region, often referred to as the "diffusion-limited" region, the measured redox plateau output currents 315 are responsive to the rate of glucose diffusion into and across the membrane and are not responsive to the input potential, thus the four different glucose sample concentrations are readily observed.

To the left of the $E_{plateau}$ line 310, thus at input potentials lower than the plateau oxidation potential of the reduced mediator, the output currents change in response to the glucose concentration of the sample and also in response to changes in the input potentials. In this potential region, where output currents are responsive to input potential, the system is operating in the kinetic potential region 320 of the reduced mediator as the output currents are not only responsive to the rate of diffusion into the membrane as in a diffusion-limited system operating at an input potential at or greater than the plateau oxidation potential of the redox mediator, but also are responsive to the degree to which the reduced mediator is oxidized, as unlike in the diffusion-limited system, not all of the reduced redox mediator is oxidized. For the described osmium-complex mediator, the kinetic potential region 320 occurs between approximately −0.15 V to +0.15 V; however, this region would be different for different redox mediators. Input potentials higher than 0.15 V would gradually approach the plateau oxidation potential of the osmium mediator, which begins at approximately 0.175 V against an Ag/AgCl reference.

As shown by the $E_{Low}$, $E_{eq}$, and $E_{Hi}$ vertical lines residing within the kinetic potential region 320 of the redox mediator, different output currents are produced for the same sample glucose concentration as all the reduced mediator has not yet been oxidized by the input potential. Unexpectedly, the measured output currents increase with increasing potential in an approximately linear fashion as the reduced mediator is oxidized, thus providing a rising slope from regression. The $E_{Low}$, vertical line represents a situation where the ratio of reduced redox mediator to oxidized redox mediator is greater than 1, meaning there is more reduced redox mediator than oxidized redox mediator, while the $E_{eq}$ line represents the situation where the concentration of reduced redox mediator and oxidized mediator are substantially equal. The $E_{Hi}$ line represents a situation where the ratio of reduced redox mediator to oxidized redox mediator is less than 1, meaning there is more oxidized than reduced redox mediator present at and near the working electrode surface.

The kinetic potential region includes a range of input potentials centered at $E_{eq}$, where the measured output current increases substantially linearly with increasing input potential and is proportional to $(E-E_{eq})$ at a fixed analyte concentration, thus providing a rising slope (RS, nA/mV). In the absolute potential scale, the current is proportional to the potential. In a wider range of input potentials centered at $E_{eq}$ the current is proportional to $\exp(E-E_{eq})$, meaning some curvature may develop in the relationship between output current and input potential extending outside the $E_{Low}$, and $E_{Hi}$ lines, as governed by an exponential as opposed to linear function. This wider range of input potentials retains an increasing relationship between output currents and input potentials, or the i-V curve, but may depart from substantial linearity where there is little oxidized in relation to reduced mediator and when the input potential approaches the plateau oxidation potential as there is little reduced in relation to oxidized mediator. The input potential used to provide the kinetic potential region 320 may be continually varied, varied with multiple increasing steps, e.g., "step voltammetry", and the like—provided that the desired test sensor sensitivity and linearity or exponentially of the output currents to the input potentials are obtained.

Figure 3B:
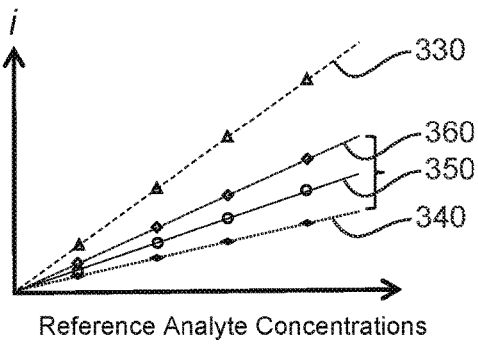
FIG. 3B represents output currents that would be obtained at four different analyte concentrations (Y-axis) in relation to the four known sample analyte concentrations (X-axis).

FIG. 3B represents output currents that would be obtained at four different analyte concentrations (Y-axis) in relation to the four known sample analyte concentrations (X-axis). Line 330 includes a single output current for each of four known analyte concentrations obtained from the plateau oxidation potential region 315 in FIG. 3A, thus as would be measured at and after the input potential exceeds the plateau oxidation potential of the reduced mediator, such as represented by line 310 of FIG. 3A. Thus, for each of the four sample analyte concentrations, a single output current value would be produced in the plateau oxidation potential, thus diffusion-limited region, regardless of the input potential. This would allow for a simple correlation between a single measured output current and a known analyte concentration.

Lines 340, 350, and 360 show currents as would be measured from the kinetic potential region 320 of FIG. 3A, where the line 340 includes a current value for each known sample analyte concentration at $E_{Low}$, the line 350 includes a current value for each known sample analyte concentration at $E_{eq}$, and the line 360 includes a current value for each known sample analyte concentration at $E_{Hi}$. While FIG. 3B is representative for clarity, linearity was found between $E_{Low}$ current values at different known sample analyte concentrations, the $E_{eq}$ current values at different known sample analyte concentrations, and the $E_{Hi}$ current values at different known analyte concentrations.

Thus, as with the line 330 and the associated expected linearity in output currents from different sample analyte concentrations obtained from the diffusion-limited region, lines 340, 350, and 360 provide linearity in the output currents from different sample analyte concentrations obtained from the non-diffusion-limited kinetic potential region 320. Although not as simple as the line 330 situation where a single current value corresponds to a single sample analyte concentration, one or more of the current values forming lines 340, 350, and 360 may be directly correlated with the sample analyte concentration when any one of these input potentials is selected.

Furthermore, having the ability to select from more than one input potential in the kinetic potential region of the redox mediator to produce different output currents provides the ability to regulate or "tune" test sensor sensitivity with the input potential. For example, upon subcutaneous insertion the input potential corresponding to line 340 may be preferred due to the high relative sensitivity of the test sensor, while during the normal lifespan of the test sensor the input potential corresponding to line 350 may be preferred, while as the test sensor nears the end of its useful life the input potential corresponding to line 360 may be preferred due to the low relative sensitivity of the test sensor.

This is the case as after insertion test sensor sensitivity tends to be "high" for a relatively short duration, "normal" for a relatively long duration, and then "low" for a relatively short duration as the inserted test sensor nears the end of its useful life. In this way a more constant test sensor sensitivity is maintained during the time of the CGM analysis by selecting the desired input potential throughout the total insertion lifetime of the test sensor. Additionally, the lower input potentials of the kinetic potential region in relation to the plateau oxidation potential region can significantly extend the useful life of the subcutaneously inserted test sensor as less demand is put on the enzyme and mediator, in addition to reducing the rate at which the pores of the membrane are blocked and the rate at which the redox material of a counter-reference electrode is depleted—if the test sensor is so equipped. Such "sensitivity tunability" also may be advantageous when the same sensitivity is desired across different test sensors or batches of test sensors having variances in manufactured sensitivity.

Figure 4:
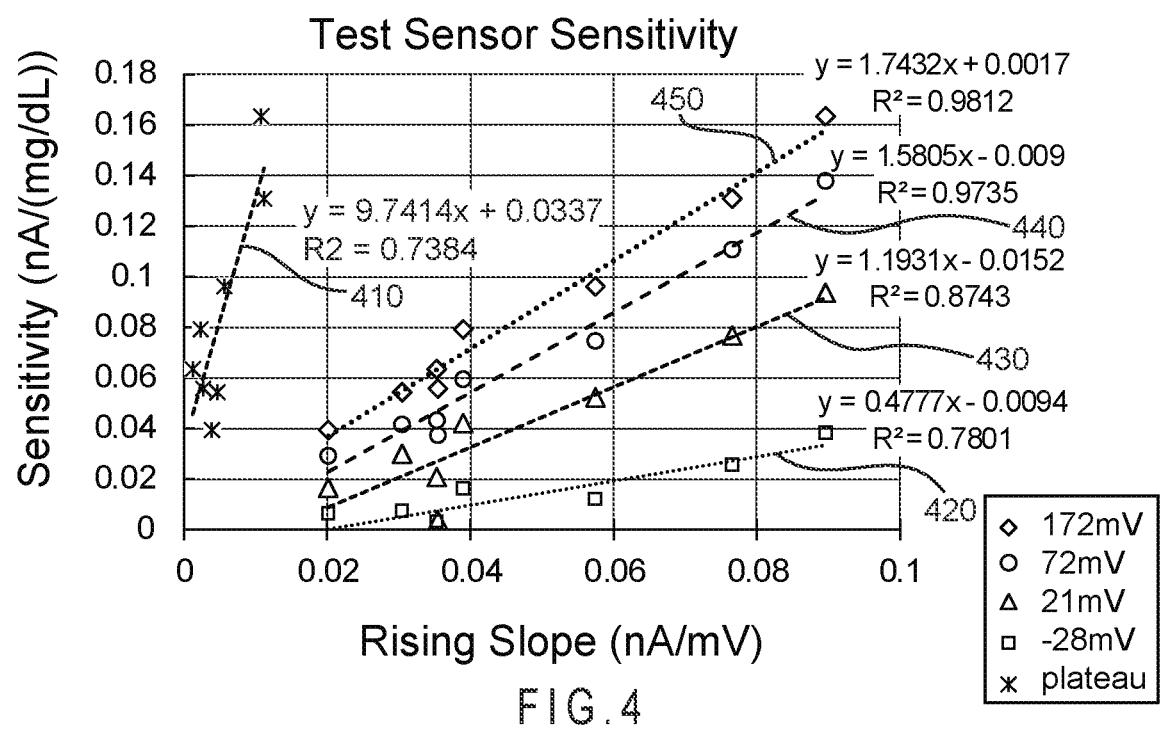
FIG. 4 provides test sensor sensitivity data obtained from test sensors at a known laboratory glucose concentration of 90 mg/dL with the same type of test sensor from both the diffusion-limited potential region and the kinetic potential region by discrete "step voltammetry".

FIG. 4 provides test sensor sensitivity data obtained from test sensors at a known laboratory glucose concentration of 90 mg/dL with the same type of test sensor from both the diffusion-limited potential region and the kinetic potential region by discrete "step voltammetry". Sensitivity is represented in output current nanoamps (nA) over glucose concentration in (mg/dL) on the Y-axis, while output current (nA) over input potential (mV) is represented on the X-axis, providing a rising slope (RS, nA/mV) for each sensor. Greater numerical RS values on the X-axis relate to greater sensitivity of the test sensor. Lines 420, 430, 440, and 450 were determined at different input potentials and provide different correlations with the RS values, as discussed further below.

Relationship 410 was obtained from the plateau oxidation potential region at an input potential of approximately 0.18 V to 0.22 V, hence within the approximately +0.17 V to about +0.3 V plateau oxidation potential region of the osmium-complex based redox mediator. For relationship 410, RS was calculated using the output currents from the input potentials of +0.175 V and +0.22 V in the plateau oxidation potential region. The nearly vertical relationship having a rising slope of 9.7414 establishes that little change in output currents occurs in response to changing input potentials in the plateau oxidation potential region as expected.

Relationships 420, 430, 440, and 450 were obtained at input potentials lower than the plateau oxidation potential of the reduced mediator, thus at input potentials of –0.028 V, +0.021 V, +0.072 V, and +0.172 V, respectively. The obtained $R^2$ values show that the input potentials used to obtain the 430, 440, and 450 relationships show sufficient linearity to reside within the kinetic potential region in addition to having an increasing relationship between the input potentials and output currents. While some of the kinetic potential region sensitivity values are below the 0.04 lowest sensitivity value of the plateau oxidation potential region, the sensitivity values of the kinetic potential region relationships show progressively lower sensitivity range (0.04 to 0.16 on the Y-axis) compared to sensitivity values obtained from the plateau oxidation potential region due to the lower input potentials. The gentle rising slope increases of the kinetic potential region relationships (0.47, 1.19, 1.58) in relation to the near order-of-magnitude greater rapidly rising slope of the plateau oxidation potential relationship (9.74) also establish that changes in input potential in the kinetic potential region provide significant control over the sensitivity of the analysis.

While it is understandable to think that the sensitivity of a biosensor should always be maximized, this is not the case for CGM biosensors in our opinion. This is true in our opinion because individual CGM sensors may have different sensitivity due to the nature of sensor composition and manufacturing process. In addition, CGM sensor sensitivity over long duration subcutaneous insertion may vary up and down due to multiple factors that vary with the specific conditions present at the insertion site and the test sensor itself. When inserted subcutaneously the sensitivity of the test sensor is often quite high initially. This behavior may be related to changes in the membrane of the test sensor, such as expansion of the membrane, or other factors. The sensitivity of the inserted test sensor often then decays with insertion time of up to about twenty hours to reach an equilibrium state of a normal sensitivity. This normal sensitivity operating period for the test sensor then extends for several hours, often around ninety, until test sensor sensitivity starts to decline as the enzyme deactivates.

In addition to enzyme deactivation, the redox mediator may lose its activity, the redox material at a counter-reference electrode may be overly consumed to lose its original pseudo-reference potential, and/or the pores in the membrane may become blocked. Thus, it can be advantageous to control the sensitivity of a manufactured sensor after insertion by selecting a different input potential to achieve the desired sensitivity based on the sensor's manufactured sensitivity at a fixed potential, and the subcutaneous insertion lifespan of the test sensor. It may also be advantageous to provide an increasing input potential to counterbalance the general trend of test sensor sensitivity decline.

Figure 5A:
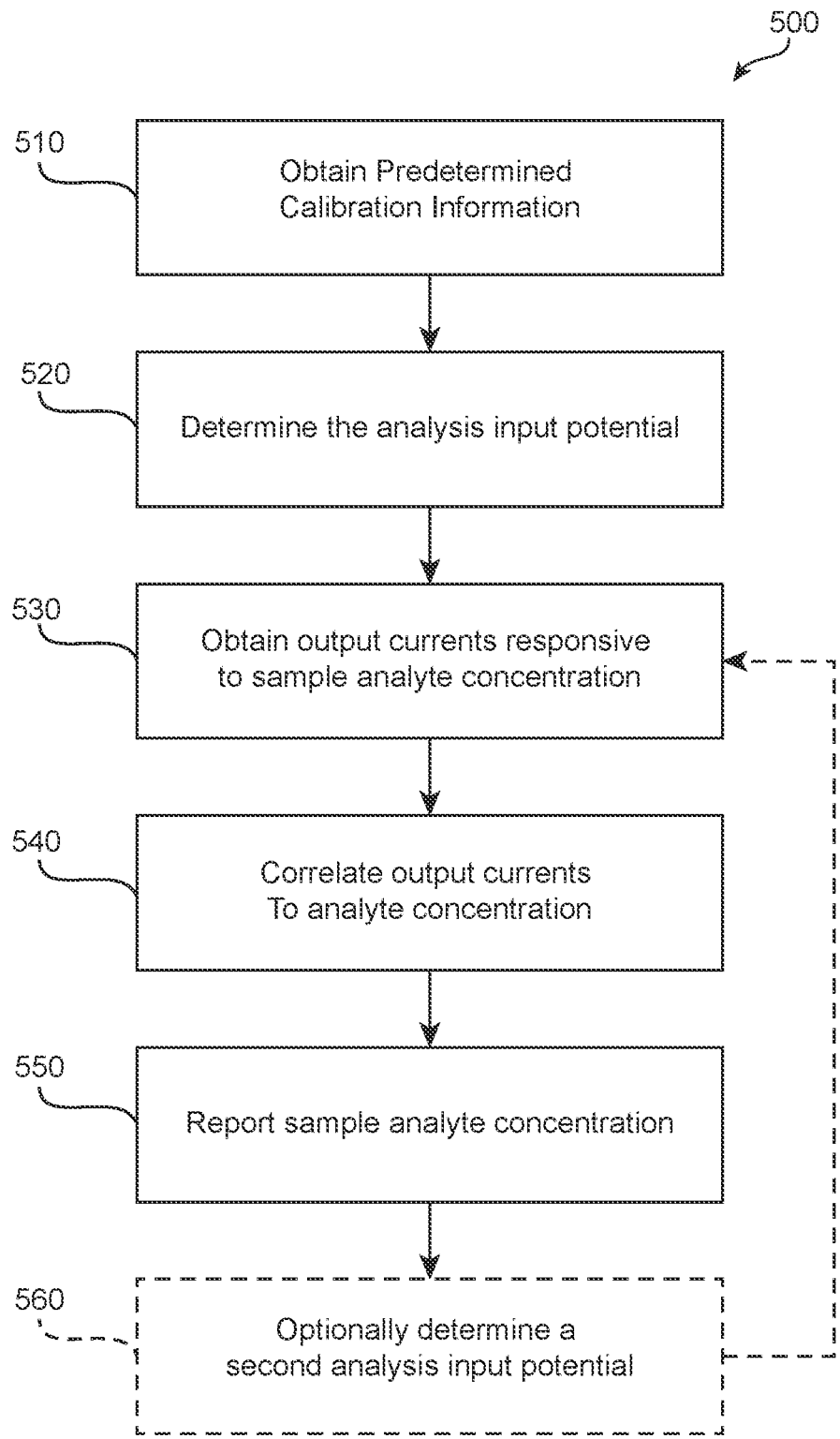
FIG. 5A represents a method of subcutaneously determining the glucose concentration of a subject with an inserted test sensor.

FIG. 5A represents a method 500 of subcutaneously determining the glucose concentration of interstitial fluid of a subject with an inserted test sensor. In the method 500 the analysis input potential resides within the kinetic potential region of the test sensor's redox mediator and the analysis input potential is selected based on the sensitivity of the test sensor at the calibration input potentials. The selected analysis input potential will be lower than the high calibration input potential if the sensitivity at the high calibration input potential is greater than the desired sensitivity, and vice versa. Starting the analysis at a relatively low input potential that increases with insertion time provides the benefits of a relatively short delay before determining analyte concentration and prolongs the useful lifespan of the subcutaneously inserted test sensor.

In obtain predetermined calibration information 510, the measurement device determines a code from the test sensor and obtains predetermined laboratory calibration data for the test sensor. The predetermined laboratory calibration data includes an input potential ramping routine, may optionally include an initial input potential, and may optionally include instruction to alter the calibration input potentials for a specific manufacturing lot of test sensors. The input potential ramping routine or routines and optional initial input potential are determined in the laboratory before subcutaneous insertion of the test sensor and are based on the redox potential of the redox mediator. The predetermined laboratory calibration data may include additional information useful for the measurement device to perform the analysis.

Figure 6A:
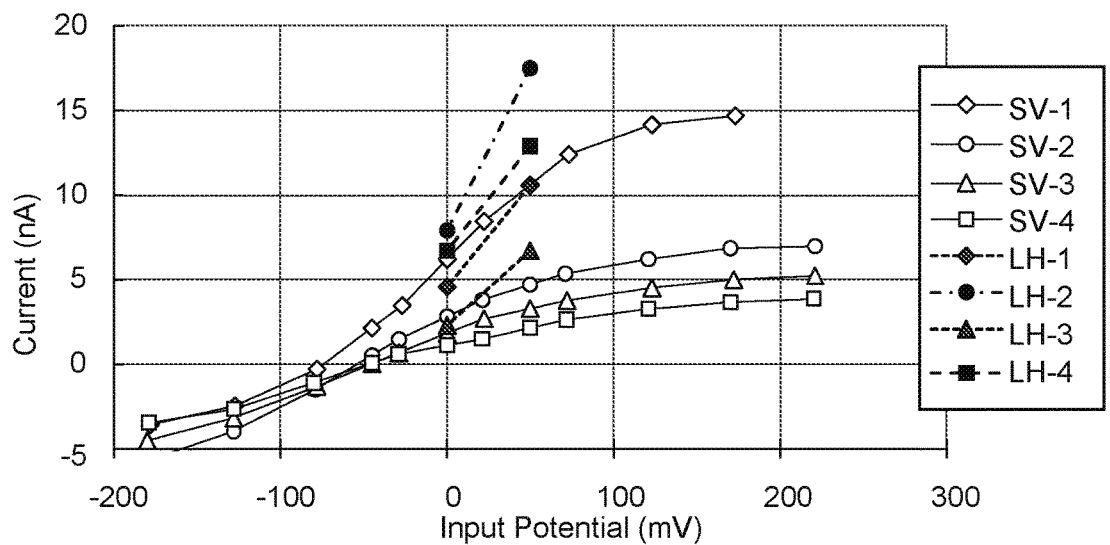
FIG. 6A shows the output currents obtained from the osmium-complex mediator at varying input potentials with a 90 mg/dL known laboratory glucose sample concentration for multiple test sensors.

FIG. 6A shows the output currents obtained from the osmium-complex mediator at varying input potentials with a 90 mg/dL known laboratory glucose sample concentration for multiple test sensors. The known laboratory glucose concentration may be determined gravimetrically, with a reference instrument, such as a YSI 2300 STAT PLUT glucose analyzer, or with a BGM device such as the Contour NEXT and the Contour NEXT ONE BGM devices as available from Ascensia Diabetes Care, Parsippany, NJ. Lines SV1-SV4 provide the output currents obtained for the four different test sensors at the same 90 mg/dL known laboratory glucose concentration. From the figure, the SV-1 line establishes that this test sensor has a much higher sensitivity than the SV-2 through SV-4 test sensors.

While the overall linearity performance of the i-V curve from the −0.2 V to +0.18 V range is relatively poor for the osmium-complex mediator, superimposed on the graph are the values of the output currents obtained at a "low" 0 V and a "high" +0.05 V for each test sensor. While in this instance 0 V and +0.05 V potentials were chosen as "low" and "high" calibration input potentials, other low and high calibration input potentials may be used that reside within the kinetic potential region of the mediator. Similarly, low, medium, and high calibration input potentials that reside within the kinetic potential region may be used.

The low and high calibration input potentials residing within the kinetic potential region of the redox mediator will be different for redox mediators having a different kinetic potential region than the discussed osmium-complex redox mediator. For example, for the osmium-complex mediator the kinetic potential region is from approximately −0.15 V to +0.15 V, thus the selected low of 0 V and high of +0.05 V reside within the kinetic potential region of the osmium-complex redox mediator.

The kinetic potential region of a redox mediator generally is a 0.15 to 0.3 V range of potentials starting approximately 0.05 V below the beginning of the plateau oxidation potential of the redox mediator. For example, for the oxygen/hydrogen peroxide redox mediator, 0.55 V vs. a Ag/AgCl reference electrode may be considered the beginning of the plateau oxidation potential. Thus, for the oxygen/hydrogen peroxide redox mediator, the upper end of the kinetic potential region that would extend from 0.2 to 0.5 V, hence 0.05V lower than the 0.55 V plateau oxidation potential. In the case of ferrocene monocarboxylic acid, 0.35 V vs. Ag/AgCl may be considered the beginning of the plateau oxidation potential region. Thus, for the ferrocene monocarboxylic acid redox mediator, the kinetic potential region would be expected to extend from 0.15 V to 0.3 V, hence 0.05 V lower than the 0.35 V plateau oxidation potential.

Quasi-reversible and reversible redox mediator systems would have narrower kinetic potential regions than the nearly irreversible redox mediator systems, such as oxygen/hydrogen peroxide. Thus, in contrast to the osmium-complex mediator, the low and high calibration input potentials could be 0.3 V and 0.4 V for the oxygen/hydrogen peroxide redox mediator. Similarly, for the ferrocene monocarboxylic acid redox mediator, the low and high calibration input potentials could be 0.2 V and 0.25 V.

Lines LH1-LH4 result from the low and high calibration input potential output currents for different test sensors LH1-LH4, respectively. The rising slope of the LH1-LH4 lines provide an indicator of the sensitivity of each individual test sensor under the conditions of the analysis, with more rapidly rising (numerically greater) slopes reflecting more sensitive test sensors. Thus, of the four test sensors LH-1-LH-4, LH-2 is the most sensitive, while LH-3 is the least sensitive.

Figure 6B:
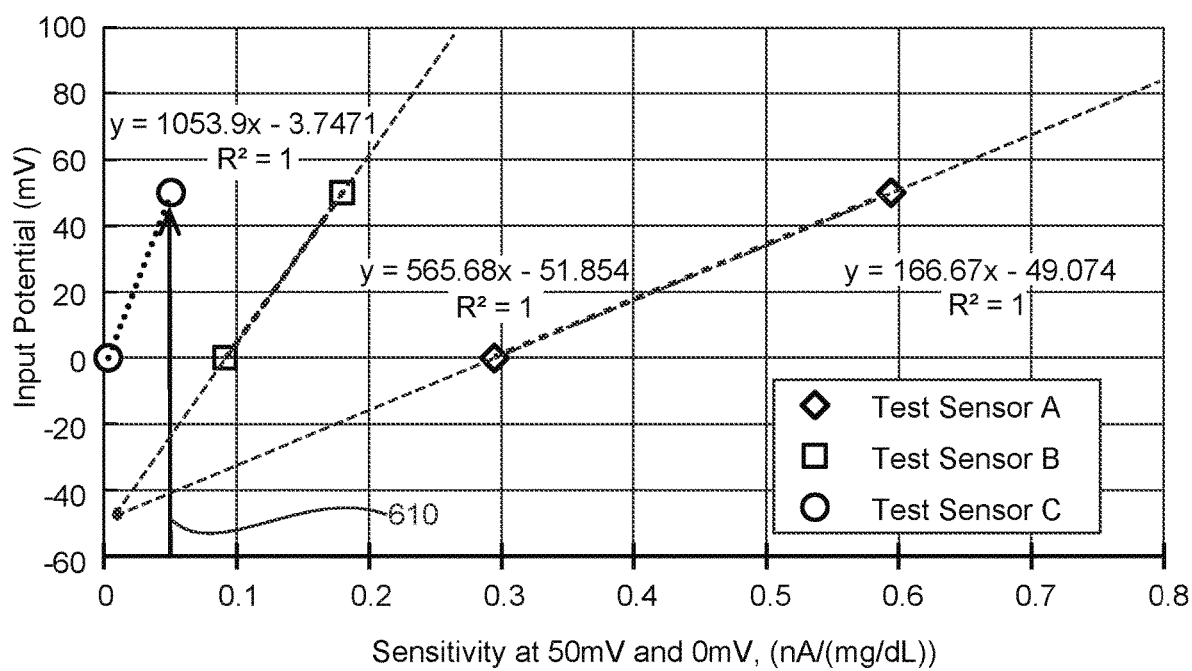
FIG. 6B shows different test sensor sensitivities obtained by plotting calibration input potentials against the test sensor sensitivities for three different test sensors (A, B, C).

FIG. 6B shows different test sensor sensitivities obtained by plotting calibration input potentials against the test sensor sensitivities for three different test sensors (A, B, C). The lines in this plot were plotted from data similar to the LH-1-LH-4 lines in FIG. 6A. The selected high and low calibration input potentials (+0.05 V, 0 V) reside within the kinetic potential region of the redox mediator. The sensitivity for each of the three different test sensors were determined by dividing the output currents measured at the high and low calibration input potentials by the known laboratory glucose concentration of 90 mg/dL.

When the three relationships for Test Sensors A, B, and C are compared, test sensor A has a slope of 167, test sensor B has a slope of 566, and test sensor C has a slope of 1054. From this it can be determined that at the known laboratory glucose concentration, test sensor A is significantly more sensitive than test sensor C (meaning that the change from high to low calibration input potential in in the y-axis causes a wider range of sensitivity change in the x-axis), with test sensor B falling in the approximate middle. Preferably, at least one output current value is recorded for the low and high calibration input potentials, however this at least one recorded output current may be a single measured output current value or a combination, such as through averaging, of more than one measured current value at the low and high calibration input potentials.

Vertical line 610 placed on the figure reflects a selected, thus desired sensitivity at which to perform the sample analysis, regardless of which test sensor is used to perform the analysis. At the selected sensitivity (0.05 nA/(mg/dL)) shown by this vertical line, the vertical line intersects the sensitivity relationship of test sensor A at −0.041 V, the sensitivity relationship of test sensor B at −0.024 V, and the sensitivity relationship of test sensor C at +0.049 V. Hence, to provide the selected sensitivity for the analysis, these are the input potentials that provide approximately the same analysis sensitivity for each test sensor. This data is summarized below in Table I where high and low are the calibration input potentials, the determined sensitivity value is provided at the high and low calibration input potentials, and the analysis input potential for each test sensor is determined to provide the selected sensitivity of 0.05 nA/(mg/dL) to the analysis. Mathematically, the initial input potential for each test sensor may also be determined by $V = \text{Slope} * S_{target} + \text{Intercept}$. For instance, $$V_{sensorA} = 166.67 * 0.05 - 49.074 = -40.7 \text{ mV}.$$

TABLE I

| Sensor | High Cal. IP | Low Cal. IP | Sens. at High Cal. IP | Sens. at Low Cal. IP | Slope | Analysis Input Potential |
|---|---|---|---|---|---|---|
| A | +50 mV | 0 mV | 0.594 | 0.294 | 166.67 | −0.041 V |
| B | +50 mV | 0 mV | 0.180 | 0.092 | 565.68 | −0.035 V |
| C | +50 mV | 0 mV | 0.051 | 0.004 | 1053.9 | +0.049 V |

From Table I it can be seen that at the selected sensitivity of 0.05 the determined analysis input potentials show a similar increase in degree when compared to the slopes determined for each test sensor using the high and low calibration input potentials. Thus, at the high calibration input potential of +50 mV the manufactured sensitivity of test sensor C is 0.051 nA/(mg/dL), while that of test sensor A is 0.594 nA/(mg/dL), greater than an order of magnitude difference. Similarly, the input potential determined to provide the selected analysis sensitivity for test sensor C is +0.049 V while the input potential determined to provide the selected analysis sensitivity for test sensor A is only −0.041 V— a significant difference that results in the two test sensors performing substantially the same during an analysis. Thus, the ability to determine input potentials in the kinetic potential region of the redox mediator allows manufactured sensitivity variance to be equalized for different test sensors.

Table I also demonstrates the principle of altering the input potential in the kinetic potential region of the redox mediator to achieve the selected sensitivity for the analysis. If the sensitivity of a test sensor at the high calibration input potential as manufactured is higher than the selected sensitivity desired for the analysis, the input potential for the analysis may be adjusted lower than the calibration input potential. This sensitivity adjustment is not possible when the sensor is operated in the plateau oxidation potential region where the output currents are independent of the input potential. Thus, varying the input potential in the kinetic potential region of the redox mediator may be used to reduce or "tune out" variances in manufactured sensitivity between different test sensors in latter use and to "tune" a specific inserted test sensor as desired for an analysis.

Figures 6C, 6D:
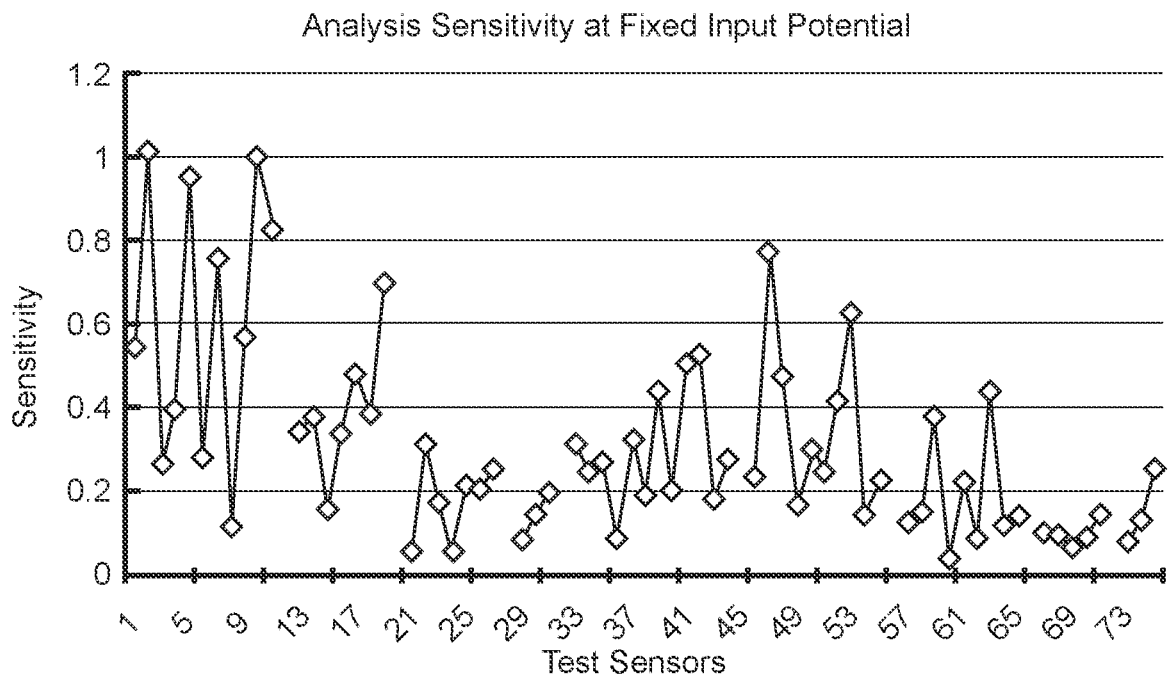
FIG. 6C provides the test sensor sensitivity of 73 test sensors in response to a fixed 0.05 V input potential at the known laboratory glucose concentration of 90 mg/dL.
FIG. 6D provides the sensitivity for the same 73 test sensors when the input voltage applied to each test sensor is altered in accord with a selected sensitivity as previously described in relation to FIG. 6B.

FIG. 6C and FIG. 6D establish the effectiveness of this technique of selecting input potentials to provide substantially similar analysis sensitivity for a batch of test sensors having varying manufactured sensitivity at the known laboratory glucose concentration of 90 mg/dL. FIG. 6C provides the test sensor sensitivity of 73 test sensors in response to a fixed 0.05 V input potential and shows a standard deviation of 0.266 between the sensitivity values. FIG. 6D provides the sensitivity for the same 73 test sensors when the input potential applied to each test sensor is altered in accord with a selected sensitivity as previously described in relation to FIG. 6B. As established by FIG. 6D, with the input potential applied to each sensor based on the FIG. 6B sensitivity, the 73 test sensors now provide a similar analysis sensitivity with a standard deviation between the sensitivity values of only 0.017. Hence, an approximate 94% reduction in sensitivity standard deviation was provided by altering the input potential applied to each test sensor in accord with a selected sensitivity as previously described in relation to FIG. 6B.

Figure 7A:
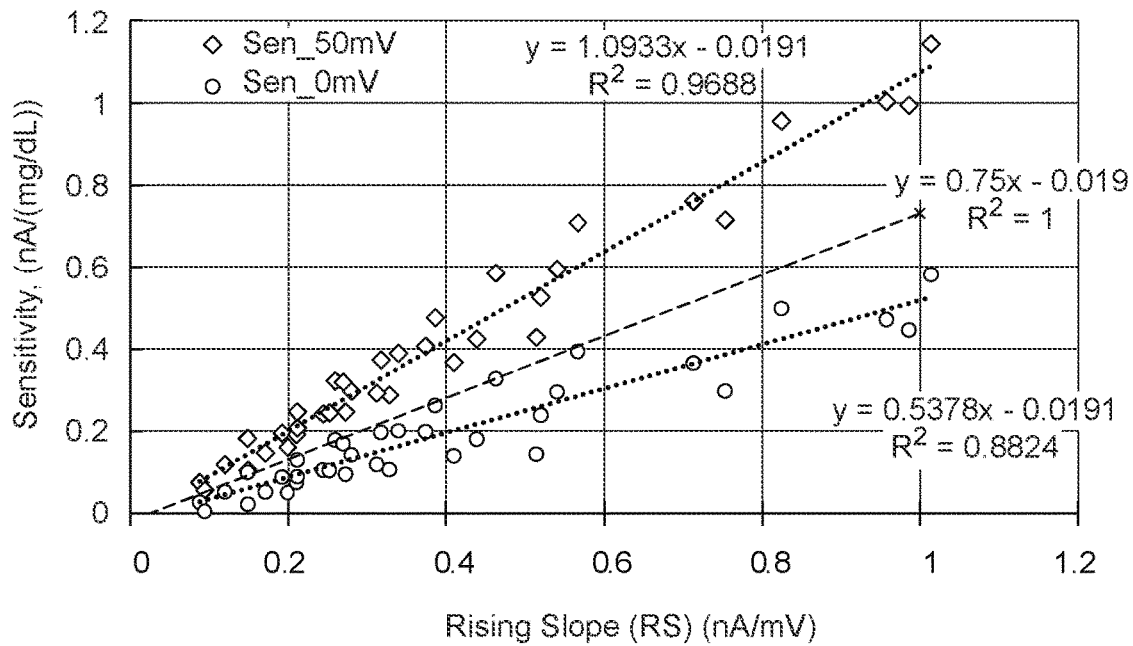
FIG. 7A shows the +0.05 V and 0 V sensitivity data (current/glucose) for multiple test sensors.
Figure 7B:
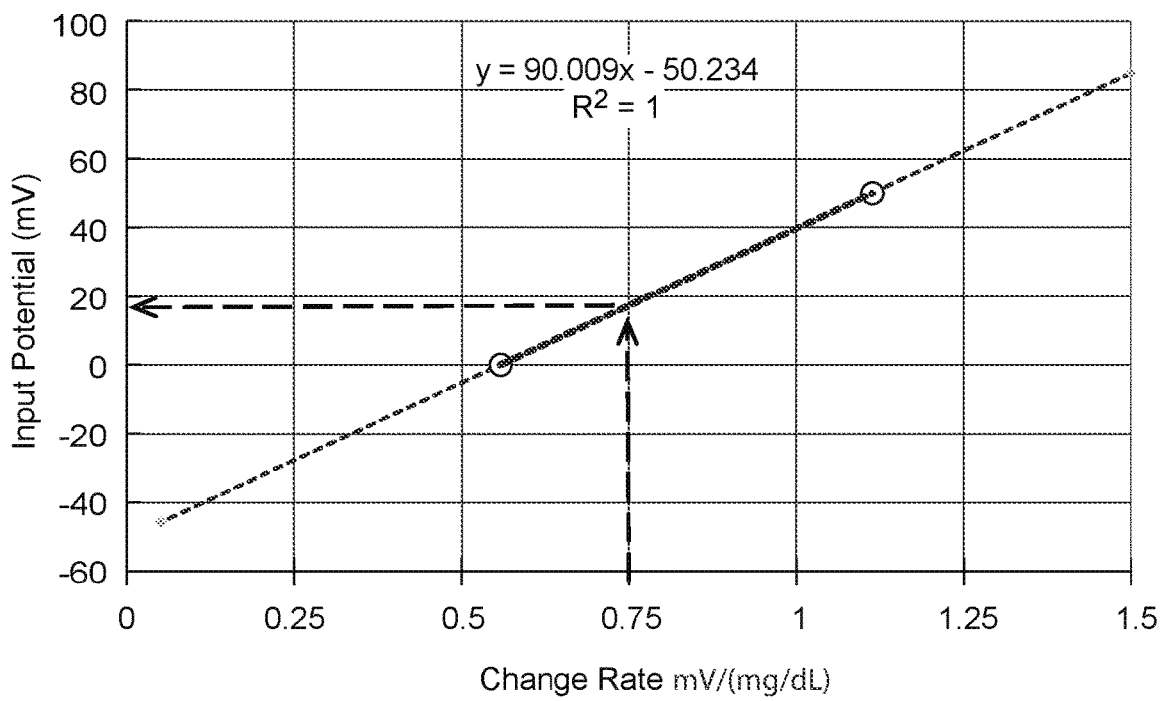
FIG. 7B plots these two slopes or "change rates" from FIG. 7A against the high and low input potentials of +0.05 V and 0 V to obtain a relationship, such as the depicted line.

FIGS. 7A and 7B show an alternate way of predetermining the desired input potential based on a single test sensor of a manufactured batch in the laboratory, but unlike the FIG. 6 method this method relies on a batch of test sensors in determining the input potential to equalize the variability in manufactured sensitivity. FIG. 7A plots sensitivity against RS values using +0.05 V and 0 V obtained sensitivity data (output current/known laboratory or BGM determined reference glucose concentration) for multiple test sensors. Thus, each diamond represents a sensitivity determined at the high calibration input potential of +0.05 V from an individual test sensor while each circle represents a sensitivity determined at the low calibration input potential of 0 V for the same test sensor.

The high calibration input potential obtained sensitivities are then converted to a relationship (y=1.0933x−0.019) by regression to obtain a change rate (CR) of 1.093 mV/(mg/dL), while the low calibration input potential obtained sensitivities provided a change rate (CR) of 0.5378 mV/(mg/dL) from the relationship y=0.5378x−0.0191. The change rate may be thought of as the change rate of test sensor sensitivity versus RS. Thus, the low and high calibration input potential regression relationships internalize the change rate of sensitivities vs. RS determined from multiple as opposed to a single test sensor as previously described in relation to FIG. 6B.

A single test sensor having a RS value of 0.0922 nA/mV was then selected to determine its appropriate initial input potential in view of the multiple test sensors for operation at a selected sensitivity of 0.05 nA/(mg/dL). Together these numbers provide a "pair point" of (0.0922, 0.05). A second pair point was created at 0 with the intercept of the low and high calibration input potential regression relationships, thus (0, −0.019). These two pair points were then used to mathematically determine a pair point relationship of y=0.75x−0.0191, thus having a change rate (CR) in mV/(mg/dL) of 0.75 and the same intercept of −0.019 as the low and high calibration input potential regression relationships. For this single test sensor, this relationship resides between the low and high calibration input potential regression relationships for the multiple test sensors, but this is not required.

FIG. 7B shows a change rate relationship determined by plotting the low (0 V) and high (+0.05 V) calibration input potentials against the change rates for the sensitivity versus RS values of the low and high calibration input potential regression relationships of FIG. 7A. This new relationship is y=90.009x−50.234 as shown in the figure. The CR of 0.75 for the single test sensor is then used with the new relationship to determine an initial input potential of +0.17 V for the single test sensor that will equalize its sensitivity with the multiple test sensors used to generate the high and low calibration input potential sensitivity versus RS relationships of FIG. 7A.

Mathematically, the initial input potential for the single test sensor may be determined by solving the equation y=90.009*0.75−50.234 mV. This determination is represented graphically in FIG. 7B, where a vertical line at 0.75 CR interests with the new relationship and a horizontal line intersecting with the y-axis provides the initial input potential of 0.17 V. This initial input potential for a single test sensor optionally may be obtained by the measurement device as discussed in the context of the obtaining the predetermined calibration information 510, as previously discussed.

Figure 8A:
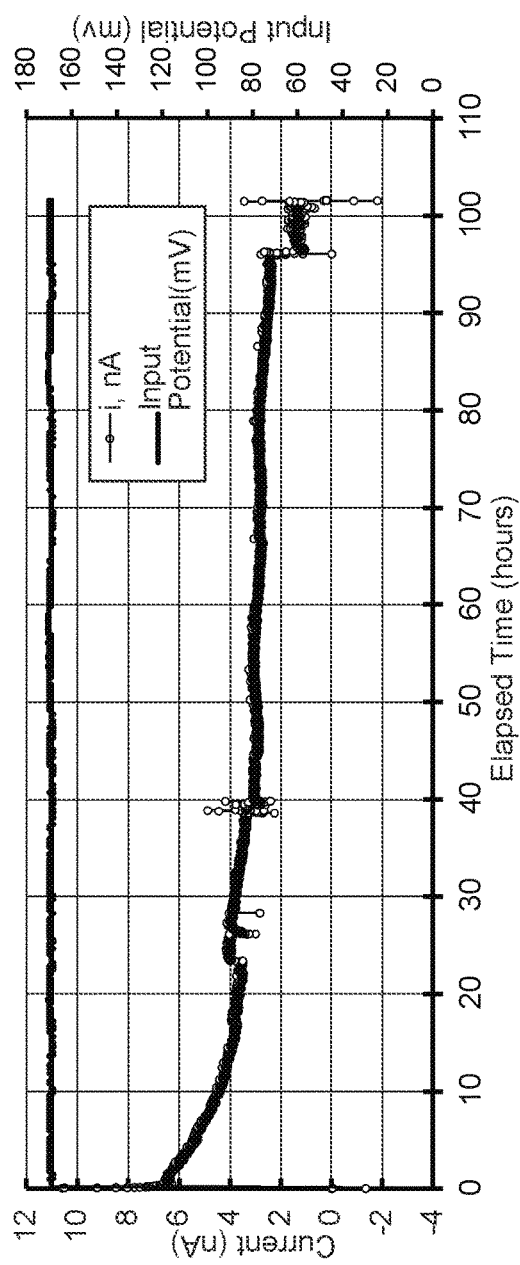
FIG. 8A depicts a response curve obtained at a fixed diffusion-limited region input potential of 0.175 V from 0 to 100 hours at a 90 mg/dL known laboratory glucose concentration.

FIG. 8A depicts a response curve obtained at a fixed diffusion-limited region input potential of 0.175 V from 0 to 100 hours at a 90 mg/dL known laboratory glucose concentration. The observed initial output current decay behavior is typical of a subcutaneously inserted test sensor operated at an input potential within the plateau oxidation potential region of the redox mediator.

The output currents start high in response to the fixed potential at the plateau oxidation potential of the reduced mediator and then decline over an approximately forty-hour period while reaching a substantially stable output current of 3 nanoamps (nA). A relatively sharp decline is observed from 0 to approximately 15 hours as the sensitivity of the test sensor rapidly decreases after insertion. During this initial rapid decline in the output currents in relation to the fixed input potential it is necessary to provide some type of correction to the system to obtain relevant sample analyte concentrations from the inserted test sensor, as the substantially stable output current of 3 nA has not yet been reached.

This uncertainty of the relationship between the output currents and the analyte concentration during the initial rapid decline of test sensor sensitivity results in a relatively long delay between test sensor insertion and the generation of accurate analyte sample concentrations.

An input potential ramping routine is developed by applying the plateau oxidation potential of the redox mediator, a low or high calibration input potential, a different input potential within the kinetic potential region of the redox mediator, or a combination of these potentials to one or more test sensors at a known laboratory glucose concentration and measuring the resulting output currents over a duration of time. Preferably, multiple potentials and multiple test sensors are used to provide output current decays.

FIG. 8A shows this being done over an approximately 100-hour period for a single test sensor using the plateau oxidation potential of the redox mediator. The measured output currents may then be analyzed to determine the percent of current decay at selected times, such as 0.5, 1, 4, 12, and 20 hours. Based on the determined percentages of current decay at the selected times, the input potential ramping routine may be determined with a curve-fitting method, such as a polynomial or other mathematical technique. Instead of determining the percent of current decay at selected times, the input potential ramping routine also may be developed by using a curve-fitting method to curve-fit the output currents.

Figure 8B:
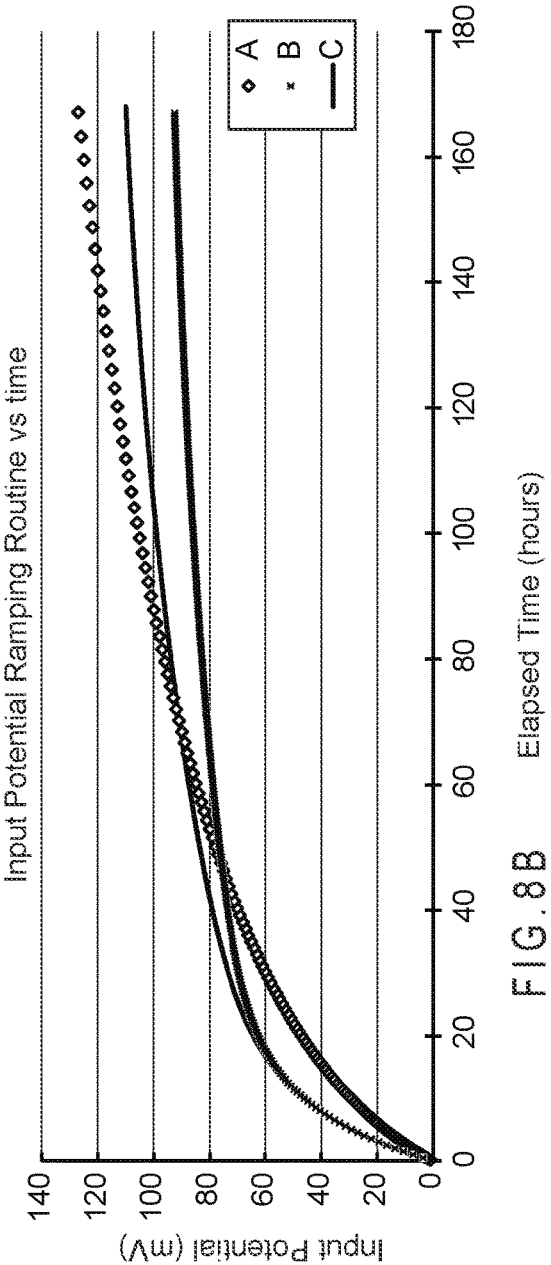
FIG. 8B represents example input potentials (A, B, C) varied with test sensor insertion time by an input potential ramping routine to provide a continually increasing input potential and to reduce the issues caused by the initial output current decline and the terminal output current decline previously described in relation to FIG. 8A.

FIG. 8B represents example input potentials (A, B, C) varied with test sensor insertion time by an input potential ramping routine to provide a continually increasing input potential and to reduce the issues caused by the initial output current decline and the terminal output current decline as previously described in relation to FIG. 8A. An input potential ramping routine is preferably applied in addition to the determined analysis input potential for a test sensor. As represented in FIG. 8B, the input potential ramps relatively rapidly from 0 to 40 hours (corresponding with the previously observed relative rapid decline in test sensor sensitivity), thus maintaining analysis sensitivity even while test sensor sensitivity decreases. While more difficult to see in the figure, the rate of input potential increase also increases around the 80-hour time to maintain analysis sensitivity during the terminal decline in test sensor sensitivity.

The ramping increase in analysis input potential may be linear in relation to time, curved in relation to time, linear and curved in relation to time, and the like. The ramping increase in analysis input potential may have one or more segments of significant change, such as by 0.02 V to 0.06 V. Preferably, a significant change in the analysis input potential occurs within the first 20 hours of test sensor insertion with a second significant change occurring during the next 80 to 120 hours or more of insertion. Other time durations for a significant change in the analysis input potential may be used. Thus, the input potential ramping routine and hence the rate at which the initial input potential is ramped within the kinetic potential region of the redox mediator during the CGM analysis is preferably predetermined in the laboratory during the obtain the predetermined calibration information 510.

In determine an analysis input potential 520, the measurement device provides high and low calibration input potentials to the test sensor, such as the +0.05 V and 0 V potentials used during the obtain a predetermined calibration information 510 or different high and low calibration potentials, and measures the output currents so an analysis input potential similarly may be determined by the measurement device as previously described in relation to FIG. 6B.

The high and low calibration input potentials may be applied to the inserted test sensor for a time of 1 to 30 minutes, 10 to 20 minutes, or preferably 1 to 10 minutes, for example. The time that the high calibration input potential is applied to the inserted test sensor is preferably the same as the time that the low calibration input potential is applied to the inserted test sensor; however, this is not required.

However, unlike for the prior obtain the predetermined calibration information 510 performed in the laboratory, as the test sensor is subcutaneously inserted during the determine the analysis input potential 520, the determine the analysis input potential 520 is based on the output currents measured from the single inserted test sensor. Also, to determine the current/glucose sensitivity values a reference analyte concentration is determined by the user with a single-use disposable test sensor BGM system. Preferably, for glucose analysis, the user determines the reference glucose concentration with the BGM system within 20 minutes, preferably within 10 minutes of initiation of the determine the analysis input potential 520.

Thus, during the determine the analysis input potential 520 the output currents measured at the high and low calibration input potentials and the reference glucose concentration determined by the user with the BGM system are used to determine a regression sensitivity relationship similarly to any one of the test sensor lines represented in FIG. 6B. More than one BGM system reading may be used. A desired sensitivity is then selected by the measurement device and used to determine a corresponding analysis input potential within the kinetic potential region of the redox mediator as also previously described in relation to vertical line 610 of FIG. 6B.

Figure 5B:
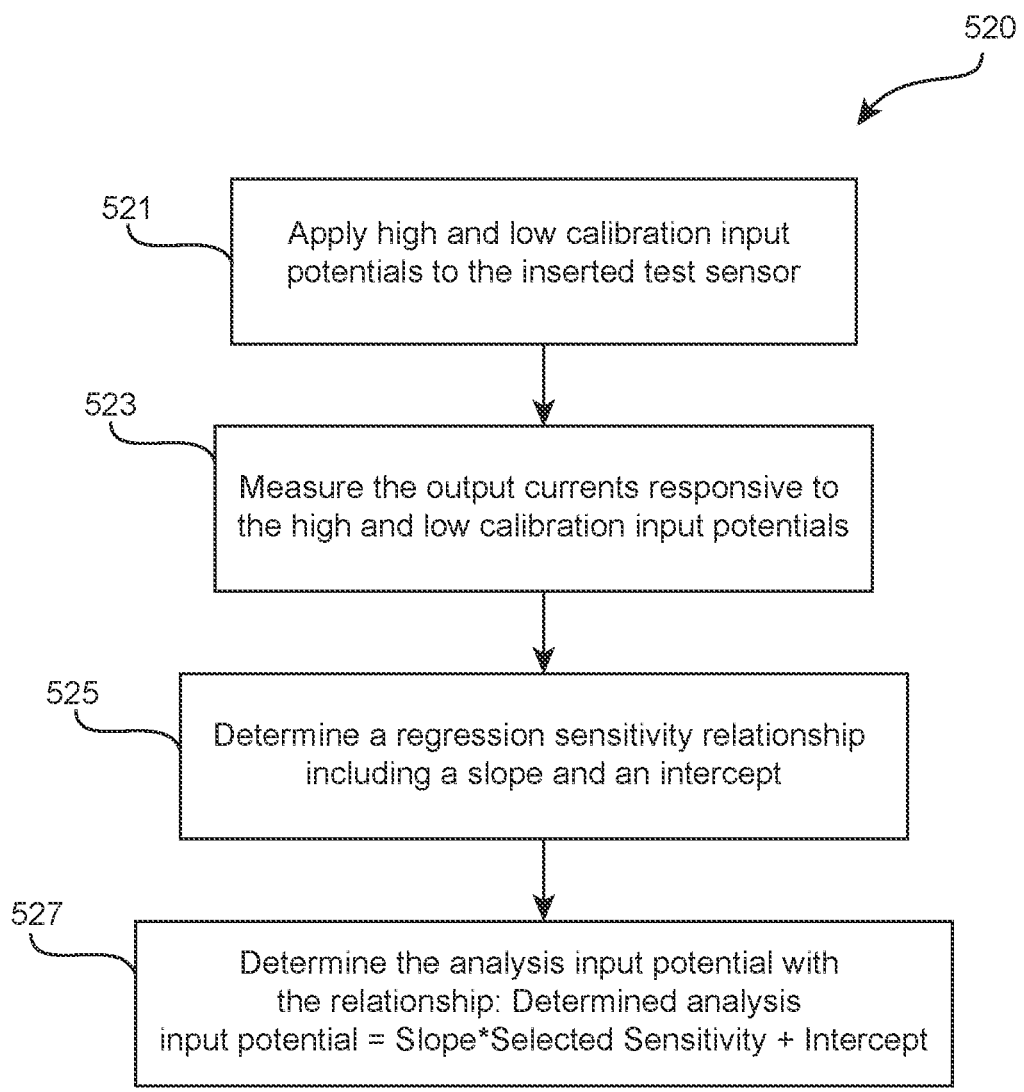
FIG. 5B represents a "mathematical" method of determining the analysis input potential for determining the glucose concentration of a subject with an inserted test sensor.

FIG. 5B represents a method 520 that may be used to determine the analysis input potential using the relationship:

Determined analysis input potential=Slope*Selected Sensitivity+Intercept

As previously discussed, in 521 the high and low calibration input potentials are applied to the inserted test sensor by the measurement device. In 523 the measurement device measures the output currents responsive to the high and low calibration input potentials. In 525, the measurement device then determines a regression sensitivity relationship by modifying, preferably through divisions, the measured output currents by the BGM system determined reference glucose concentration and performing regression. The regression sensitivity relationship provides a slope and intercept. In 527, the measurement device then determines the analysis input potential by multiplying a selected sensitivity value for the analysis by the determined slope and adding the intercept. The slope and the intercept are taken from the regression sensitivity relationship. As the regression sensitivity relationship will have a positive slope, the intercept is added.

Once the analysis input potential 520 is determined, the measurement device then applies the inserted test sensor determined analysis input potential in the kinetic potential region of the redox mediator to the inserted test sensor as modified by the input potential ramping routine previously determined during the obtain predetermined calibration information 510 in the laboratory.

Figure 9:
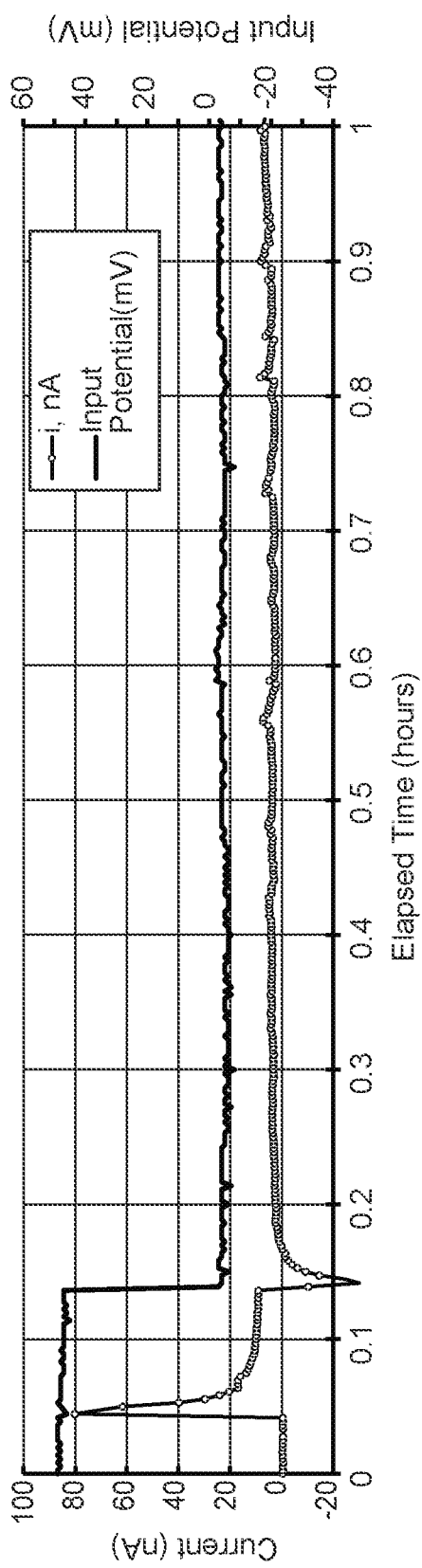
FIG. 9 provides an example of the high and low +0.05 V and 0 V calibration input potentials applied to the test sensor after subcutaneous insertion that permit for the desired analysis input potential within the kinetic potential region of the mediator to be determined by the measurement device.

FIG. 9 provides an example of the high and low+0.05 V and 0 V calibration input potentials applied to the test sensor after subcutaneous insertion that permit for the desired analysis input potential within the kinetic potential region of the mediator to be determined by the measurement device. The calibration input potentials induced the positive and negative current spikes. In this example, the determined analysis input potential happened to be 2 mV lower than the second step potential at 0 V. (not shown).

Thus, there is a substantially seamless transition from the second step of the calibration process to the ramping routine starting at −2 mV. This analysis input potential determination preferably is completed within 0.1 to 0.3 hours of test sensor insertion. This is a substantial improvement in relation to the plateau oxidation potential system as discussed in the context of FIG. 8A where approximately 15 hours of insertion time was required for the system to stabilize.

Thus, the method 500 addresses the conventional problem of a relatively long test sensor insertion time having to pass before output currents are obtained from the test sensor that provide accurate analyte concentration values. For example, when the conventional plateau oxidation system of FIG. 8A is compared with the kinetic potential system of the method 500 of FIG. 9, output currents that could be accurately correlated with a known laboratory glucose concentration were not obtained until after approximately 15 hours in FIG. 8A, while output currents that could be accurately correlated with the known laboratory glucose concentration were obtained after approximately 10 minutes in FIG. 9—an approximate two order of magnitude improvement in time to obtain accurately correlatable output currents. The method 500 preferably provides accurately correlatable output currents within 3 hours of test sensor insertion, more preferably within 1 hour of test sensor insertion, and most preferably within 30 minutes of test sensor insertion.

In obtain output currents responsive to sample analyte concentration 530, the measurement device repeatedly applies the analysis input potential determined in 520 as modified by the input potential ramping routine to obtain output currents responsive to the sample analyte concentration. The analysis input potential preferably is applied to the test sensor continually, but the output currents are measured with a selected frequency, such as every 0.1, 0.2, 0.5, 1, 5, 10, or twenty minutes. If the analysis input potential is not continually applied to the test sensor, longer or shorter durations between the applications of the analysis input potential to the test sensor by the measurement device may be used.

Figure 10:
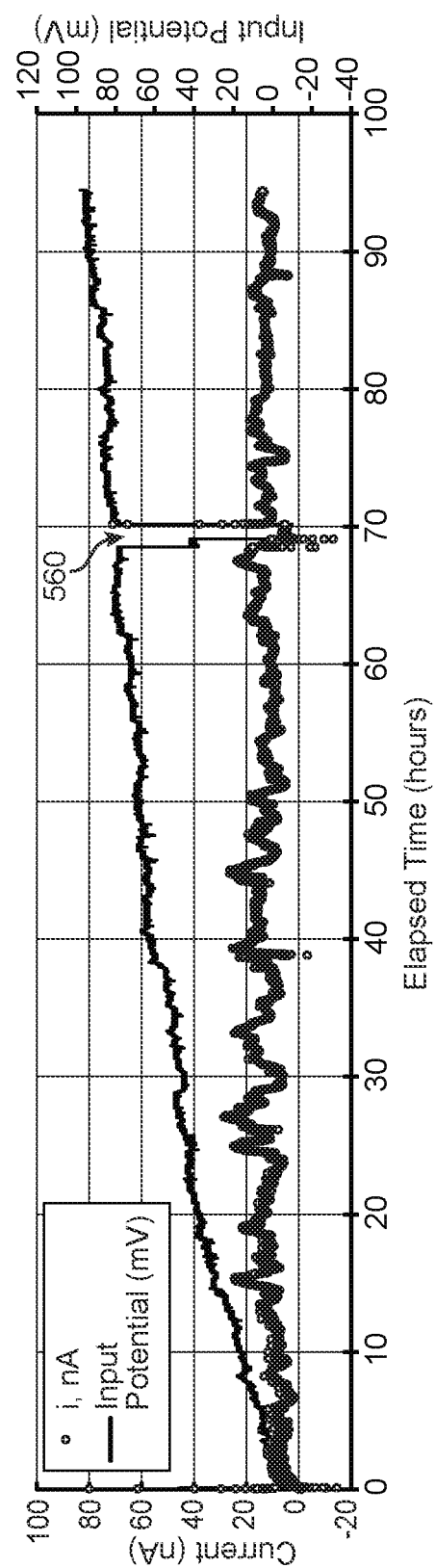
FIG. 10 is a time-expanded version of FIG. 9 and provides an example of the analysis input potential applied to the inserted test sensor within the kinetic potential region of the redox mediator by the measurement device over an approximately 90-hour analysis time.

FIG. 10 is a time-expanded version of FIG. 9 and provides an example of the analysis input potential applied to the inserted test sensor within the kinetic potential region of the redox mediator by the measurement device over an approximately 90-hour analysis time. As can be seen from the figure, while the analysis input potential (top line) is ramping to higher potentials, the output currents measured from the test sensor by the measurement device (lower line) are relatively flat. The figure also establishes that the useful life of the inserted test sensor has not been reached at 90-plus hours as the output currents remain relatively flat past 90-minutes. Thus, in addition to providing approximately level output currents between 0 and 20 nA—hence providing similar analysis sensitivity regardless of changing test sensor sensitivity during insertion, the method also extends the useful life of the inserted test sensor.

In correlate output currents to analyte concentration 540, the measurement device determines the analyte concentration of the sample from the output currents responsive to the analyte concentration of the sample. Preferably, the measured output currents are converted into sample analyte concentrations using a conversion function, such as a power function, a non-linear function defined by a polynomial, or another mathematical technique that correlates the measured current values to the sample analyte concentration. The measurement device may combine, such as through averaging, multiple measured output currents to improve the accuracy and/or precision of the CGM analysis.

In report sample analyte concentration 550, the measurement device reports the determined analyte concentration of the sample to a user. This may be done through wired or wireless means, preferably wirelessly to a remote computing device such as a smartphone, smartwatch, tablet, computer, and the like.

In optional determine a second analysis input potential 560, after some period the measurement device ceases to apply the analysis input potential to the inserted test sensor, thus stopping the CGM analysis. Then the measurement device provides high and low calibration input potentials of +0.05 V and 0 V to the inserted test sensor. The high and low calibration input potentials may be the same or different as those previously used in the obtain the predetermined calibration information 510 and in the determine the analysis input potential 520.

The measurement device also signals the user to provide a reference analyte/glucose concentration as obtained with a BGM system which when provided to the measurement device by the user allows for a new sensor regression sensitivity relationship to be determined. Thus, the output currents measured at the high+0.05 V and low 0 V calibration input potentials and the reference glucose concentration are again used to determine a second regression sensitivity relationship similarly to any one of the regression sensitivity relationships determined for the test sensors represented in FIG. 6B. A selected sensitivity is then used to determine a corresponding second analysis input potential within the kinetic potential region of the redox mediator. The selected sensitivity may be the same or different as used to determine the first analysis input potential. The measurement device may change the initial analysis input potential to the second analysis input potential, or maintain the initial analysis input potential as modified by the input potential ramping routine if the second analysis input potential does not exceed a threshold value, such as ±5%. Thus, in either instance, potential ramping with time is maintained.

The steps 530, 540, and 550 are then resumed to provide CGM to the user at the analysis or second analysis input potential as modified by the input potential ramping routine. FIG. 10 shows the optional 560 redetermination being performed after about 70 hours of test sensor insertion, with the analysis continuing at a higher analysis input potential with continued ramping within the kinetic potential region of the redox mediator after the optional 560 redetermination.

While the optional 560 redetermination can occur at any time after the subcutaneous insertion of the test sensor and analysis input potential determination, preferably, the optional 560 redetermination occurs after the test sensor has been inserted for 50 to 80 hours. More than one optional 560 redetermination may be performed while the test sensor is inserted.

The following examples illustrate one or more preferred embodiments of the invention. Numerous variations may be made to the following examples that lie within the scope of the invention.

EXAMPLES

Figure 11:
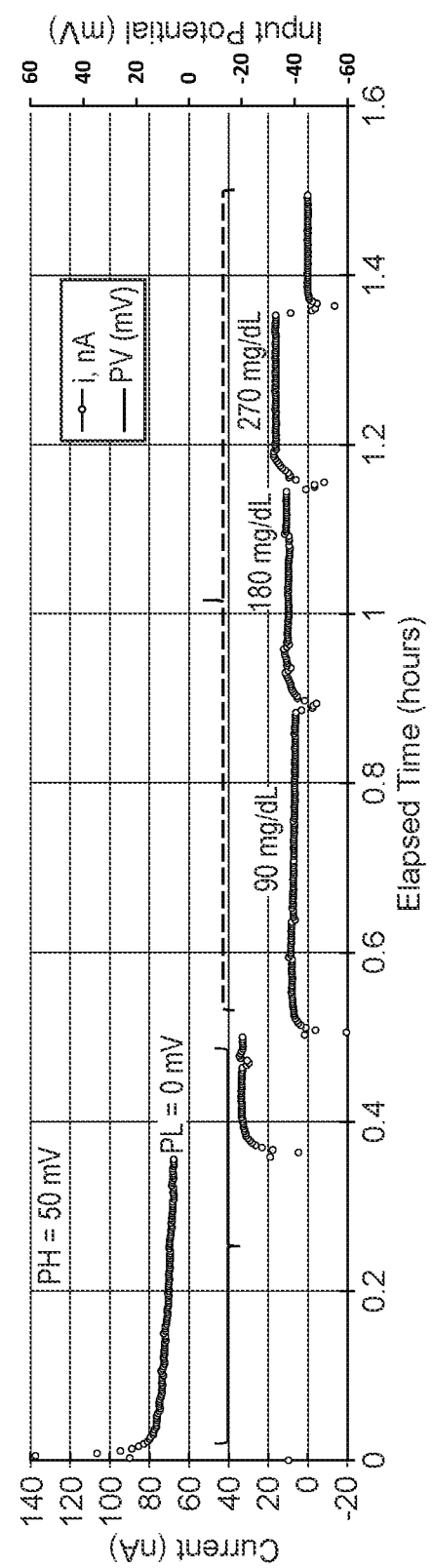
FIG. 11 plots analysis input potential and the responsive output currents measured at known laboratory glucose concentrations from a test sensor with time.

Example 1: Glucose Determination with a Test Sensor Operated in the Kinetic Potential Region of the Redox Mediator FIG. 11 plots analysis input potential and the responsive output currents measured at known laboratory glucose concentrations from a test sensor with time. The ability of the biosensor system to differentiate different glucose concentrations is established. For the first approximately half hour high (+0.05 V) and low (0 V) calibration input potentials were applied to the test sensor and an analysis input potential of approximately −0.043 V was determined. In this example, an input potential ramping routine was used, but the time duration was too short (<2 hours) to observe significant change in the analysis input potential. From approximately 0.5 hour to 0.9 hour the output currents measured at 90 mg/dL glucose are shown and are stable. The analyte concentration of the sample was then increased to 180 mg/dL and the increase in measured output currents was observed with associated stability. At approximately 1.18 hours the sample analyte concentration was increased to 270 mg/dL and again an increase in the measured output currents was observed. This demonstrates the ability of the biosensor system to generate different and stable output currents at different sample analyte concentrations in response to an analysis input potential within the kinetic potential region of the redox mediator.

Figure 12:
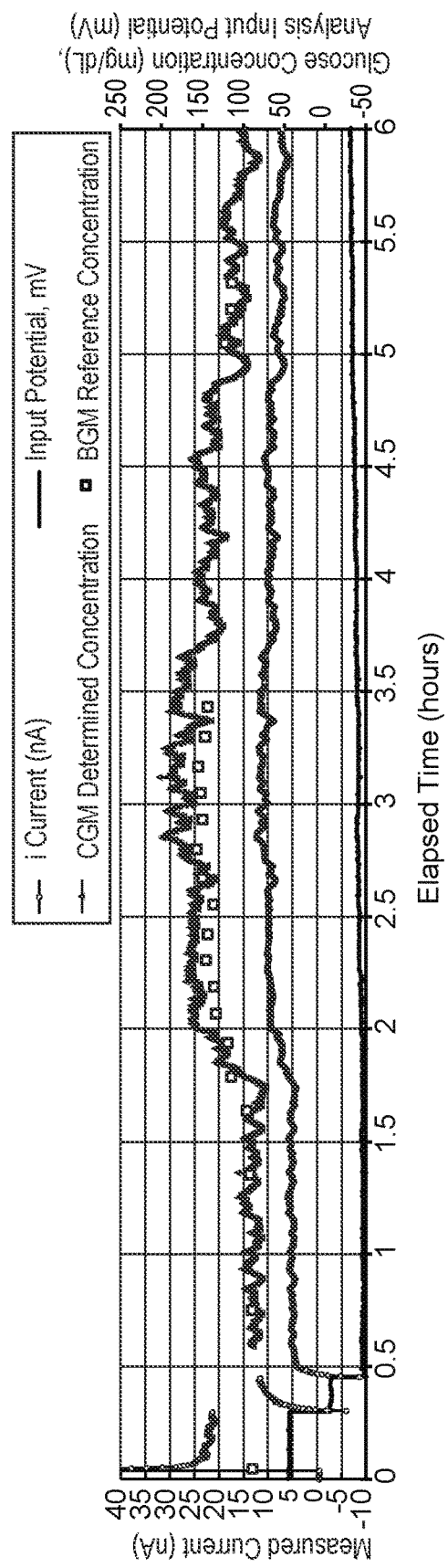
FIG. 12 plots analysis input potential and the responsive measured output currents from a test sensor with time.

Example 2: Glucose Determination with a Subcutaneously Inserted Test Sensor Operated in the Kinetic Potential Region of the Redox Mediator FIG. 12 plots analysis input potential and the responsive measured output currents from a test sensor with time. As the test sensor is subcutaneously inserted the sample glucose concentration of the human subject changes with time, thus BGM (Contour NEXT) determined reference glucose concentrations also are plotted as are the measurement device determined sample glucose concentrations. From the input potential line, the high (+0.05 V) and low (0 V) calibration input potentials were applied during the initial approximately 0.5-hour duration.

From the measured output currents test sensor sensitivities were determined by the measurement device to be 0.24 and 0.13, respectively, using the BGM determined reference glucose concentration of 89 mg/dL. Regression was then used by the measurement device to determine an analysis input potential of −0.04 V at a selected sensitivity of 0.03 nA/(mg/dL). It is also seen that the analysis input potential of −0.04 V was modified with an input potential ramping routine during the analysis as the analysis input potential increased from −0.04 V to −0.25 V over the course of the six-hour analysis time.

Approximately eight-minutes after the measurement device applied the −0.04 V analysis input potential to the test sensor, the CGM system started to report accurately correlatable output currents in relation to the BGM determined reference glucose concentration, and thus continuously provide accurate glucose concentrations. This is a substantial reduction in the subcutaneous insertion initial time delay required in relation to conventional CGM systems for accurately correlatable output currents to be measured. The analysis continued and the accuracy of the CGM system was established with the %-MARD (Mean Absolute Relative Difference) being 11.8 for the first 5 hours of the analysis.

Figure 13:
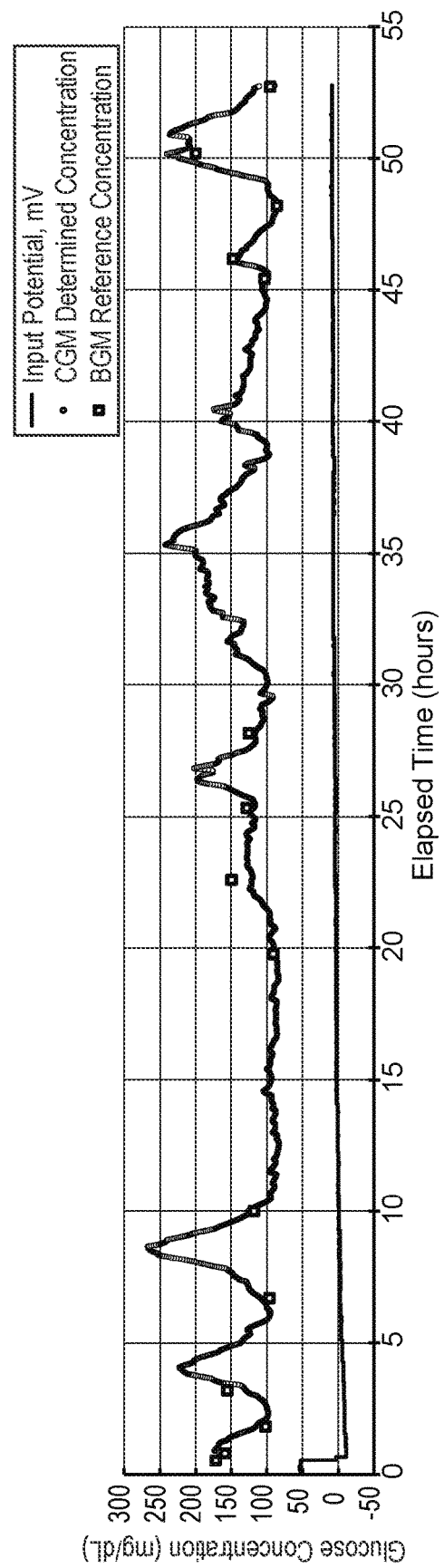
FIG. 13 plots analysis input potential and the responsive measurement device determined sample glucose concentrations from a test sensor with time.

Example 3: Long-Term Glucose Determination with a Subcutaneously Inserted Test Sensor Operated in the Kinetic Potential Region of the Redox Mediator FIG. 13 plots analysis input potential and the responsive measurement device determined sample glucose concentrations from a test sensor with time. As the test sensor is subcutaneously inserted, the sample glucose concentration of the human subject changes with time, thus BGM (Contour NEXT) determined reference glucose concentrations also are plotted. From the input potential line, the high (+0.05 V) and low (0 V) calibration input potentials were applied during the initial approximately 0.5-hour duration. The analysis input potential of −0.014 V was modified with an input potential ramping routine during the analysis as the analysis input potential increases from −0.014 V to +0.006 V over the course of the approximately 53-hour analysis time.

As seen in the measurement device determined versus BGM reference concentrations, the biosensor system was able to provide accurately correlatable output currents within 30-minutes of inserting the test sensor subcutaneously and continued to provide accurately correlatable output currents until the analysis ended. The accuracy of the CGM system was established with the %-MARD (Mean Absolute Relative Difference) being 10.2 for the approximately 53-hour analysis time.

To provide a clear and more consistent understanding of the specification and claims of this application, the following definitions are provided.

Input potential or potentials refers to the potential or voltage applied by the measurement device across the working and counter electrodes of the test sensor.

Output current or currents refers to the current measured by the measurement device across the working and counter electrodes of the test sensor in response to the input potential or potentials.

Diffusion-limited refers to the situation where a 0.01 nA or less change in output currents measured from an electrochemical redox reaction of a redox mediator at a fixed analyte concentration occurs in response to a 0.001 V change in input potential. Thus, the output currents are substantially responsive to the rate of analyte diffusion into and across the membrane enclosing the electrodes of the test sensor and not changes in the input potential.

Plateau oxidation potential refers to the minimum absolute input potential where a 0.01 nA or less change in output currents measured from an electrochemical redox reaction of a redox mediator at a fixed analyte concentration occurs in response to a 0.001 V change in input potential.

Plateau oxidation potential region refers to the region of the oxidation curve of the redox mediator where output currents are obtained from input potentials at or greater than the plateau oxidation potential of the redox mediator.

Kinetic potential region refers to a potential region of the redox mediator where output currents are responsive to changes in the input potential, thus the output currents change with changing input potential. The kinetic potential region directly contrasts with the plateau oxidation potential region of the redox mediator where the output currents are not substantially responsive to changes in the input potential. The kinetic potential region for a redox mediator preferably defines the range of input potentials where the measured output currents from the redox mediator increase positively with positive increases in input potential before the input potential reaches the plateau oxidation potential and the output currents are no longer responsive to changes in the input potential. Increase positively means an at least 0.01 nA increase in the output currents measured from an electrochemical redox reaction of a redox mediator at a fixed analyte concentration occurs in response to a 0.001 V change in input potential. Preferably, the kinetic potential region also refers to the input potential range where the measured output currents from the redox mediator increase linearly with increasing input potential before the input potential reaches the plateau oxidation potential. Increase linearly includes variances of ±10% from linearity, thus being substantially linear. The input potential range of input potentials providing increasing output currents in response to increasing input currents is somewhat broader than and encompasses the input potential range where increasing input potentials provide increasing output currents in a linear relationship.

A continually increasing input potential refers to the situation where the input potential continually increases from the analysis input potential during the duration of the analysis. The continual increase may be linear with a fixed or increasing amount per time duration or may include multiple steps where multiple output currents are measured at a first potential until the input potential is increased to a second potential where multiple more output currents are measured.

A zero potential refers to a situation where the potential is not off (open circuit), thus an output current continues to flow from the test sensor at the zero potential as the electrochemical reaction continues between the working and counter electrodes of the test sensor. A zero potential is relative in relation to a second potential, such as the fixed potential of a reference electrode.

Amperometry is an electrochemical sample analysis where current is measured at a potential (voltage) as a function of time as a potential is applied across a working and counter electrode pair of a test sensor. Amperometry measures the rate at which an electrochemically active species is being oxidized or reduced near the working electrode.

Regression refers to statistical methods used to estimate the relationship between a dependent variable and one or more independent variables. A common type of regression is linear regression that creates a "line", thus relationship, between two or more values where the line/relationship has a slope and an intercept and an error when there are more than two values. However, other forms of regression methods may be used than linear regression to relate the dependent and independent variables. A R 2 correlation coefficient may be determined that expresses how closely each of the values is to the calculated relationship when three or more values are used.

Regression sensitivity relationship refers to a relationship determined through regression that provides a slope and an intercept based on output currents modified, preferably through division, by reference analyte sample concentration.

Accurately correlatable output currents are output currents measured from a subcutaneously inserted test sensor that may be correlated with corresponding sample analyte concentrations that are within ±30%, preferably ±25%, and more preferably within ±15% of a BGM measured reference analyte concentration.

Subject refers to an animal, including, but not limited to, a primate (e.g., human, monkey, chimpanzee, gorilla, and the like), rodents (e.g., rats, mice, gerbils, hamsters, ferrets, and the like), lagomorphs, swine (e.g., pig, miniature pig), equine, canine, feline, and the like. The terms "subject" and "patient" are used interchangeably in reference, for example, to a mammalian subject, such as a human patient.

Electrical communication includes at least one of electrically connected and non-electrically connected: where electrically connected means components communicate with each other by means of a conducting path such as through a wire, a cable, other conductors, circuitry, combinations, and the like; and non-electrically connected means components communicate with each other with or without a conducting path such as with radio signals, lasers, cellular or other telephones, WIFI (wireless fidelity) or other wireless network protocols, satellites, combinations, and the like. Components with electrical communication may be both electrically connected and non-electrically connected; for example, components may be electrically connected to supply electrical power and non-electrically connected to transfer data and operating signals. "Electrical communication" also includes when components are operatively connected to perform a particular function.

Unless the context clearly dictates otherwise, where a range of values is provided, each intervening value to the tenth of the unit of the lower limit between the lower limit and the upper limit of the range is included in the range of values.

The terms "a", "an", and "the" used in the specification claims are to be construed to cover both the singular and the plural, unless otherwise indicated or contradicted by context. No language in the specification should be construed as indicating any non-claimed element to be essential to the practice of the invention.

Spatially relative terms, such as "up", "down", "top", "bottom", "right", "left", "beneath", "below", "lower", "above", "upper", and the like, may be used for ease of description to describe one element or feature's relationship to another element(s) or feature(s) as illustrated in the figures. Spatially relative terms are intended to encompass different orientations of the device in use or operation in addition to the orientation depicted in the figures. For example, if the device in the figures is turned over or rotated, elements described as "below", or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

While the present general inventive concept has been illustrated by description of several example embodiments, and while the illustrative embodiments have been described in detail, it is not the intention of the applicant to restrict or in any way limit the scope of the general inventive concept to such descriptions and illustrations. Instead, the descriptions, drawings, and claims herein are to be regarded as illustrative in nature, and not as restrictive, and additional embodiments will readily appear to those skilled in the art upon reading the above description and drawings. Additional modifications will readily appear to those skilled in the art. Accordingly, departures may be made from such details without departing from the spirit or scope of applicant's general inventive concept.

While various aspects of the invention are described, it will be apparent to those of ordinary skill in the art that other embodiments and implementations are possible within the scope of the invention.

The invention claimed is:

1. A method for determining an analyte concentration in a sample, the method comprising:
applying a first and second calibration input potentials to a subcutaneously inserted test sensor, where the first and second calibration input potentials are within a kinetic potential region of a redox mediator of the test subcutaneously inserted test sensor;
measuring output currents responsive to the first and the second calibration input potentials from the subcutaneously inserted test sensor;
determining a regression sensitivity relationship from the measured output currents responsive to the first and the second calibration input potentials;
determining a first analysis input potential within the kinetic potential region of the redox mediator from the regression sensitivity relationship;
applying the first analysis input potential to the subcutaneously inserted test sensor;
modifying a first redox state to a second redox state of the redox mediator, where a concentration of the first redox state of the redox mediator is responsive to an analyte concentration in a sample;
measuring output currents responsive to the first analysis input potential from the subcutaneously inserted test sensor;
determining the analyte concentration of the sample in response to the measured output currents responsive to the first analysis input potential; and
reporting the determined analyte concentration to a user.

2. The method of claim 1, further comprising obtaining predetermined calibration information before the applying the first and second calibration input potentials to the subcutaneously inserted test sensor.

3. The method of claim 2, where the first analysis input potential is responsive to a sensitivity of the subcutaneously inserted test sensor and to a manufactured sensitivity of multiple not-subcutaneously inserted test sensors.

4. The method of claim 2, where the predetermined calibration information includes an input potential ramping routine, an initial input potential, and the first and second calibration input potential values altered for a specific lot of test sensors.

5. The method of claim 1, where the first analysis input potential is responsive to a sensitivity of the subcutaneously inserted test sensor.

6. The method of claim 5, where the sensitivity arises from subcutaneous insertion and a manufactured sensitivity of the test sensor.

7. The method of claim 1, where the determining the regression sensitivity relationship comprises use of a reference analyte concentration of the sample.

8. The method of claim 7, where the determining the regression sensitivity relationship includes modifying the measured output currents responsive to the first and second calibration input potentials by the reference analyte concentration of the sample.

9. The method of claim 1, where the regression sensitivity relationship comprises a slope and an intercept.

10. The method of claim 9, where the determining the analysis input potential comprises using a relationship: the first analysis input potential=the slope*a selected sensitivity+the intercept.

11. The method of claim 1, where the determining the analyte concentration of the sample comprises correlating the measured output currents with the analyte concentration of the sample using a conversion function.

12. The method of claim 1, further comprising modifying the first analysis input potential with an input potential ramping routine.

13. The method of claim 1, further comprising determining a second analysis input potential, measuring output currents responsive to the second analysis input potential, and determining the analyte concentration of the sample in response to the measured output currents responsive to the second analysis input potential.

14. The method of claim 1, where the first analysis input potential continually increases after the application of the first analysis input potential to the subcutaneously inserted test sensor.

15. The method of claim 1, where the measured output currents responsive to the first analysis input potential are substantially linear.

16. The method of claim 1, where the output currents measured in response to the first analysis input potential are accurately correlatable to the analyte concentration of the sample within 30 minutes to 3 hours of subcutaneously inserting the test sensor into a subject.

17. The method of claim 1, where the redox mediator is osmium-complex based.

18. The method of claim 1, where the first analysis input potential is a lower potential than a plateau oxidation potential of the redox mediator.

19. The method of claim 1, where the first analysis input potential is determined within 0.1 to 0.3 hours of subcutaneously inserting the test sensor into a subject.

20. The method of claim 1, where movement of the analyte to working and counter electrodes of the subcutaneously inserted test sensor is non-diffusion-limited.

21. The method of claim 1, where the output currents responsive to the first analysis input potential change in response to changes in the first analysis input potential.

22. The method of claim 1, where the first and second calibration input potentials are applied to a subcutaneously inserted test sensor for 1 minute to 30 minutes after subcutaneously inserting the test sensor into a subject.

23. A method of determining an initial input potential for a test sensor based on the manufactured sensitivity of the test sensor, for performing an analysis of a sample with the test sensor, the method comprising:
    applying a first and second calibration input potentials to a test sensor contacting a sample, where the first and second calibration input potentials are within a kinetic potential region of a redox mediator of the test sensor;
    measuring output currents responsive to the first and the second calibration input potentials from the test sensor;
    determining a regression sensitivity relationship from the measured output currents responsive to the first and the second calibration input potentials using a known laboratory analyte concentration or a reference analyte concentration of the sample by modifying the measured output currents responsive to the first and the second calibration input potentials with the known laboratory analyte concentration or the reference analyte concentration of the sample;
    determining an initial input potential by multiplying a slope from the regression sensitivity relationship by a selected sensitivity and combining with an intercept from the regression sensitivity relationship.

24. The method of claim 23, where the initial input potential is incorporated into predetermined calibration information for the test sensor.

25. A method of determining an initial input potential for a test sensor based on the manufactured sensitivity of the test sensor, for performing an analysis of a sample with the test sensor, the method comprising:
    applying a first and second calibration input potentials to multiple test sensors contacting a sample, where the first and the second calibration input potentials are within a kinetic potential region of a redox mediator of the test sensor;
    measuring output currents responsive to the first and the second calibration input potentials from the multiple test sensors;
    determining a first calibration input potential regression relationship and a second calibration input potential regression relationship from the output currents measured from the multiple test sensors and a known laboratory analyte concentration or a reference analyte concentration to obtain a first calibration input potential change rate and a second calibration input potential change rate;
    determining pair point relationship for a single test sensor from a rising slope (RS) value of the single test sensor, a selected sensitivity, and the intercept of the first and second calibration input potential regression relationships;
    determining a change rate relationship from the first and second calibration input potentials and the first and second calibration input potential change rates; and
    determining an initial input potential for the test sensor from the change rate relationship and a single test sensor change rate determined from the pair point relationship.

26. The method of claim 25, where the initial input potential is incorporated into predetermined calibration information for the test sensor.

27. An analyte measurement device, comprising:
    a processor in electrical communication with a signal generator and a storage medium,
    where the processor is configured to measure output currents responsive to input potentials,
    where the signal generator is configured to provide the input potentials to working and counter electrodes of a test sensor and transferring output currents responsive to the input potentials from the test sensor to the processor;
    where the processor is configured to instruct the signal generator to apply a first and second calibration input potentials to the test sensor, where the first and second calibration input potentials are within a kinetic potential region of a redox mediator of the test sensor;
    where the processor is configured to measure output currents responsive to the first and the second calibration input potentials;
    where the processor is configured to determine a regression sensitivity relationship from the measured output currents responsive to the first and the second calibration input potentials;
    where the processor is configured to determine a first analysis input potential within the kinetic potential region of the redox mediator from the regression sensitivity relationship;
    where the processor is configured to instruct the signal generator to apply the first analysis input potential to the test sensor;
    where the processor is configured to measure output currents responsive to the first analysis input potential from the test sensor;
    where the processor is configured to determine the analyte concentration of a sample in response to the measured output currents responsive to the first analysis input potential; and
    where the processor is configured to report the determined analyte concentration to a user.

28. The analyte measurement device of claim 27, where the processor is configured to obtain predetermined calibration information and store the predetermined calibration information in the storage medium.

29. The analyte measurement device of claim 28, where the first analysis input potential is responsive to a sensitivity of the test sensor and to a manufactured sensitivity of multiple test sensors.

30. The analyte measurement device of claim 28, where the predetermined calibration information includes an input potential ramping routine, an initial input potential, and the first and second calibration input potential values altered for a specific lot of test sensors.

31. The analyte measurement device of claim 27, where the first analysis input potential is responsive to a sensitivity of the subcutaneously inserted test sensor.

32. The analyte measurement device of claim 27, where the determining the regression sensitivity relationship comprises use of a reference analyte concentration of the sample supplied by the user.

33. The analyte measurement device of claim 32, where the determining the regression sensitivity relationship includes modifying the measured output currents responsive to the first and second calibration input potentials by the reference analyte concentration of the sample.

34. The analyte measurement device of claim 27, where the regression sensitivity relationship includes a slope and an intercept.

35. The analyte measurement device of claim 34, where the determining the analysis input potential comprises using a relationship stored in the storage medium as follows: the first analysis input potential=the slope*a selected sensitivity+the intercept.

36. The analyte measurement device of claim 27, where the determining the analyte concentration of the sample comprises correlating the measured output currents with the analyte concentration of the sample using a conversion function stored in the storage medium.

37. The analyte measurement device of claim 27, where the processor is configured to modify the first analysis input potential with an input potential ramping routine stored in the storage medium.

38. The analyte measurement device of claim 27, where the processor is configured to determine a second analysis input potential, to measure output currents responsive to the second analysis input potential, and to determine the analyte concentration of the sample in response to the measured output currents responsive to the second analysis input potential.

39. The analyte measurement device of claim 27, where the processor is configured to continually increase the first analysis input potential after the applying the first analysis input potential to the test sensor.

40. The analyte measurement device of claim 27, where the output currents responsive to the first analysis input potential measured by the processor are substantially linear.

41. The analyte measurement device of claim 27, where the processor is configured to accurately correlate the output currents measured by the processor in response to the first analysis input potential to the analyte concentration within 30 minutes to 3 hours of subcutaneous insertion of the test sensor into a subject.

42. The analyte measurement device of claim 27, where the first analysis input potential is a lower potential than a plateau oxidation potential of the redox mediator.

43. The analyte measurement device of claim 27, where the processor is configured to determine the first analysis input potential within 0.1 to 0.3 hours of subcutaneous insertion of the test sensor into a subject.

44. The analyte measurement device of claim 27, where the processor is configured to apply the first and the second calibration input potentials to the test sensor for 1 minute to 30 minutes after subcutaneous insertion of the test sensor into a subject.

45. A biosensor system for determining an analyte concentration in a sample, comprising:
    a test sensor comprising working and counter electrodes and a redox mediator;
    a measurement device comprising a processor in electrical communication with a signal generator and a storage medium, where the working and the counter electrodes are in electrical communication with the signal generator;
    where the processor is configured to measure output currents responsive to input potentials from the test sensor,
    where the signal generator is configured to provide the input potentials to the working and the counter electrodes and transferring output currents responsive to the input potentials from the working and the counter electrodes to the processor;
    where the processor is configured to instruct the signal generator to apply a first and second calibration input potentials to the working and the counter electrodes, where the first and second calibration input potentials are within a kinetic potential region of the redox mediator;
    where the processor is configured to measure output currents responsive to the first and the second calibration input potentials;
    where the processor is configured to determine a regression sensitivity relationship from the measured output currents responsive to the first and the second calibration input potentials;
    where the processor is configured to determine a first analysis input potential within the kinetic potential region of the redox mediator from the regression sensitivity relationship;
    where the processor is configured to instruct the signal generator to apply the first analysis input potential to the working and the counter electrodes;
    where the processor is configured to measure output currents responsive to the first analysis input potential from the working and the counter electrodes;
    where the processor is configured to determine the analyte concentration of a sample in response to the measured output currents responsive to the first analysis input potential; and
    where the processor is configured to report the determined analyte concentration to a user.

46. The biosensor system of claim 45, where the processor is configured to obtain predetermined calibration information and store the predetermined calibration information in the storage medium.

47. The biosensor system of claim 46, where the first analysis input potential is responsive to a sensitivity of the test sensor and to a manufactured sensitivity of multiple test sensors.

48. The biosensor system of claim 46, where the predetermined calibration information includes an input potential ramping routine, an initial input potential, and the first and second calibration input potential values altered for a specific lot of test sensors.

49. The biosensor system of claim 45, where the first analysis input potential is responsive to a sensitivity of the subcutaneously inserted test sensor.

50. The biosensor system of claim 45, where the determining the regression sensitivity relationship comprises use of a reference analyte concentration of the sample supplied by the user.

51. The biosensor system of claim 50, where the determining the regression sensitivity relationship includes modifying the measured output currents responsive to the first and second calibration input potentials by the reference analyte concentration of the sample.

52. The biosensor system of claim 45, where the regression sensitivity relationship includes a slope and an intercept.

53. The biosensor system of claim 52, where the determining the analysis input potential comprises using a relationship stored in the storage medium as follows: the first analysis input potential=the slope*a selected sensitivity+the intercept.

54. The biosensor system of claim 45, where the determining the analyte concentration of the sample comprises correlating the measured output currents with the analyte concentration of the sample using a conversion function stored in the storage medium.

55. The biosensor system of claim 45, where the processor is configured to modify the first analysis input potential with an input potential ramping routine stored in the storage medium.

56. The biosensor system of claim 45, where the processor is configured to determine a second analysis input potential, to measure output currents responsive to the second analysis input potential, and to determine the analyte concentration of the sample in response to the measured output currents responsive to the second analysis input potential.

57. The biosensor system of claim 45, where the processor is configured to continually increase the first analysis input potential after the applying the first analysis input potential to the test sensor.

58. The biosensor system of claim 45, where the output currents responsive to the first analysis input potential measured by the processor are substantially linear.

59. The biosensor system of claim 45, where the processor is configured to accurately correlate the output currents measured by the processor in response to the first analysis input potential to the analyte concentration of the sample within 30 minutes to 3 hours of subcutaneously inserting the test sensor into a subject.

60. The biosensor system of claim 45, where the first analysis input potential is a lower potential than a plateau oxidation potential of the redox mediator.

61. The biosensor system of claim 45, where the processor is configured to determine the first analysis input potential within 0.1 to 0.3 hours of subcutaneously inserting the test sensor into a subject.

62. The biosensor system of claim 45, where the processor is configured to apply the first and the second calibration input potentials to the working and the counter electrodes for 1 minute to 30 minutes after subcutaneously inserting the test sensor into a subject.

\* \* \* \* \*